United States Patent
Haas et al.

(10) Patent No.: US 9,482,780 B2
(45) Date of Patent: Nov. 1, 2016

(54) MODULAR INSTRUMENTED FLOOR COVERING

(71) Applicants: Douglas D. Haas, Sparta, NJ (US); Igor Ofenbakh, Morristown, NJ (US)

(72) Inventors: Douglas D. Haas, Sparta, NJ (US); Igor Ofenbakh, Morristown, NJ (US)

( * ) Notice: Subject to any disclaimer, the term of this patent is extended or adjusted under 35 U.S.C. 154(b) by 180 days.

(21) Appl. No.: 14/471,498

(22) Filed: Aug. 28, 2014

(65) Prior Publication Data

US 2015/0374264 A1 Dec. 31, 2015

Related U.S. Application Data

(63) Continuation-in-part of application No. 14/318,035, filed on Jun. 27, 2014.

(51) Int. Cl.
| | |
|---|---|
| *G01L 1/00* | (2006.01) |
| *G01V 9/00* | (2006.01) |
| *A61B 5/11* | (2006.01) |
| *A61B 5/00* | (2006.01) |

(52) U.S. Cl.
CPC ............ *G01V 9/00* (2013.01); *A61B 5/1113* (2013.01); *A61B 5/6892* (2013.01); *A61B 5/002* (2013.01); *A61B 5/6889* (2013.01); *A61B 2560/0443* (2013.01); *A61B 2562/046* (2013.01)

(58) Field of Classification Search
CPC .... A61B 5/112; A61B 5/0022; A61B 5/002; A61B 5/6892; A61B 2562/046; A61B 5/1113; A61B 5/6889; A61B 2560/0443; A61B 5/6887; A61B 2562/0247; A61B 5/1038; G01V 9/00; G01L 1/205; G01D 5/25; E04D 3/351; E04D 1/265; E04D 3/35; E04B 7/22; G06F 3/033; G06F 3/045
USPC .......... 73/862.541, 862.044, 862.046, 862.7, 73/82.68
See application file for complete search history.

(56) References Cited

U.S. PATENT DOCUMENTS

| | | | |
|---|---|---|---|
| 5,952,585 A | 9/1999 | Haas | |
| 2009/0124938 A1* | 5/2009 | Brunner | A61B 5/1038 600/595 |
| 2012/0086659 A1* | 4/2012 | Perlin | G06F 3/005 345/173 |
| 2013/0319137 A1* | 12/2013 | Grau | G06F 3/005 73/862.381 |
| 2014/0195023 A1* | 7/2014 | Statham | A63B 69/0028 700/91 |
| 2015/0374297 A1 | 12/2015 | Haas | |

\* cited by examiner

*Primary Examiner* — Harshad R Patel
*Assistant Examiner* — Brandi Hopkins
(74) *Attorney, Agent, or Firm* — Andrew W. Ludy

(57) ABSTRACT

A modular instrumented floor covering assembly is used in connection with a subject walking across the assembly. The floor covering assembly comprises a plurality of sensor panels attached together along interlocking edges. The edges are held together by interlocking strips or by magnets. Each sensor panel has a pressure sensor matrix responsive to the weight of the subject for generating data relating to movement of the subject. The sensor panels are assembled on the floor selectively and releasably in patterns. No tools are needed for assembly. Data is sent wirelessly between the sensor panels and from the sensor panels to a computer for analysis. A power supply, wiring grid, and releasable connectors on the panel edges supplies electrical power to the sensor panels and between adjacent sensor panels.

22 Claims, 38 Drawing Sheets

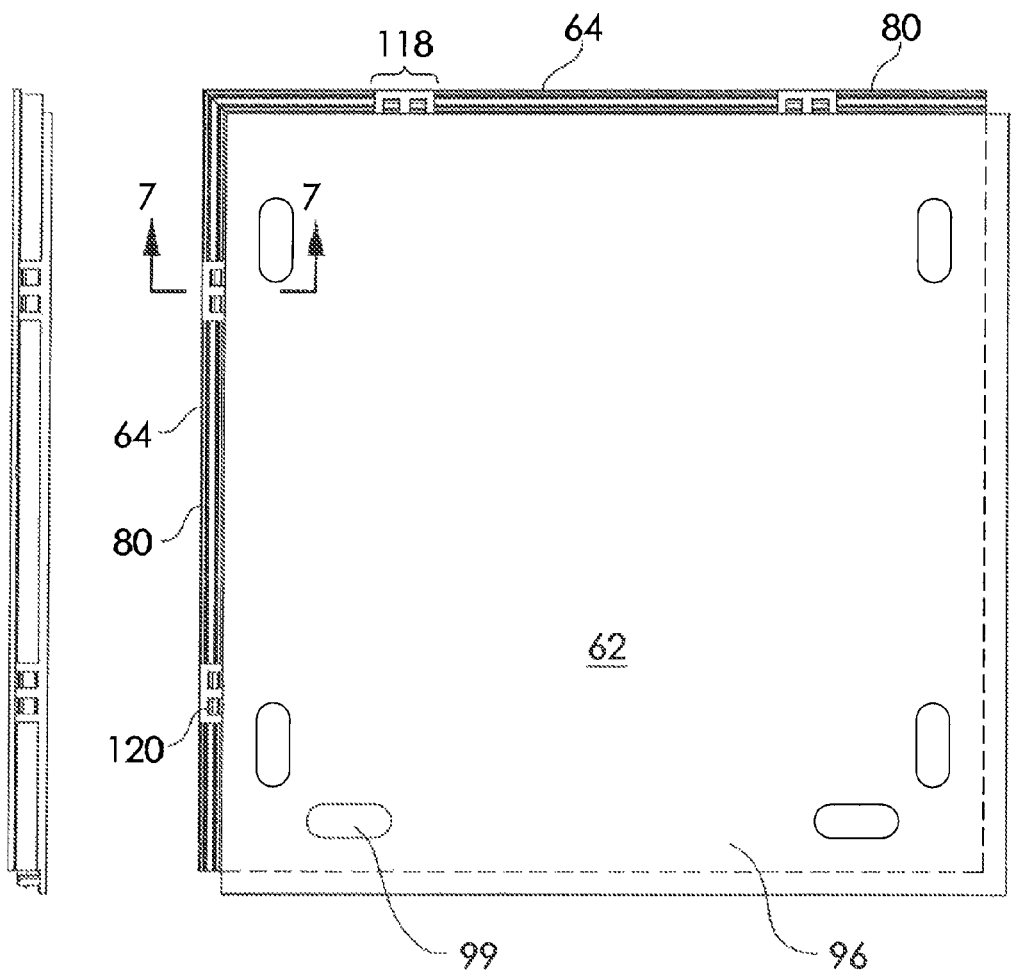

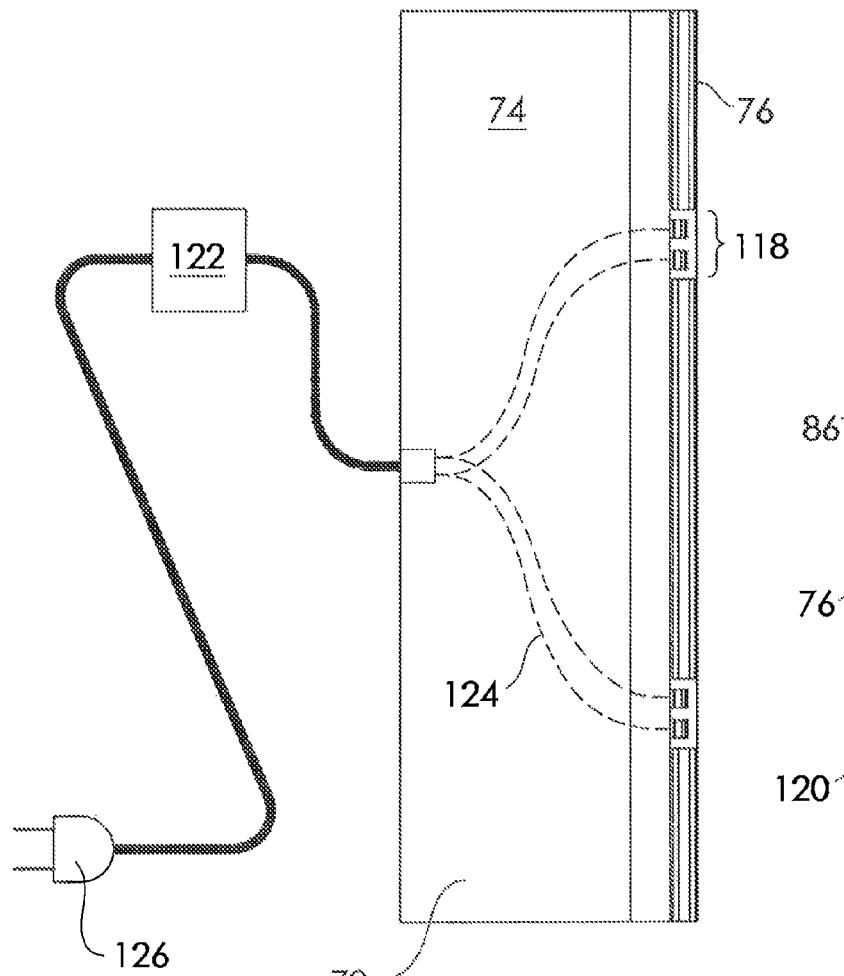
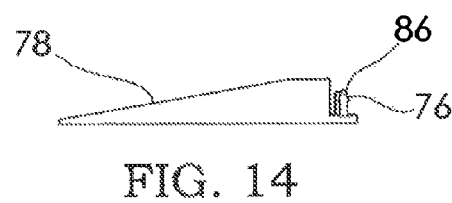
FIG. 14

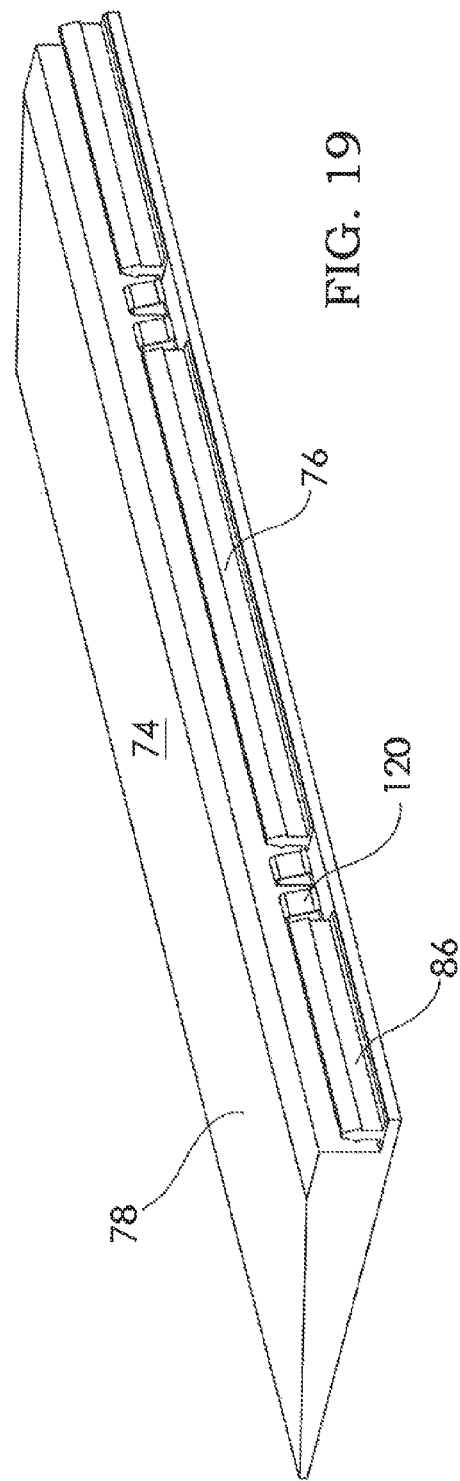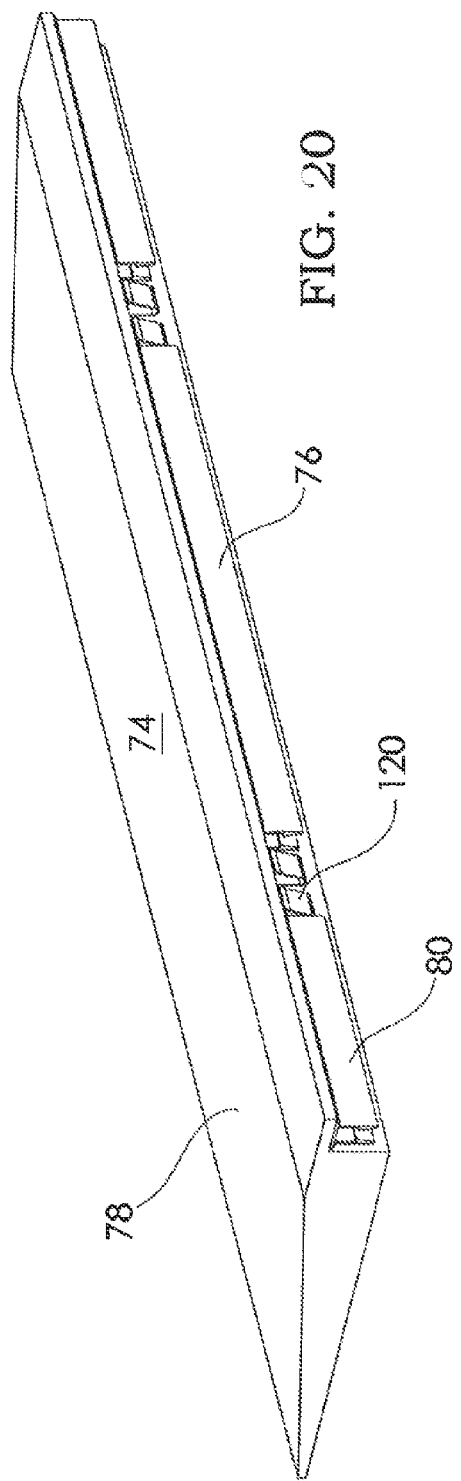

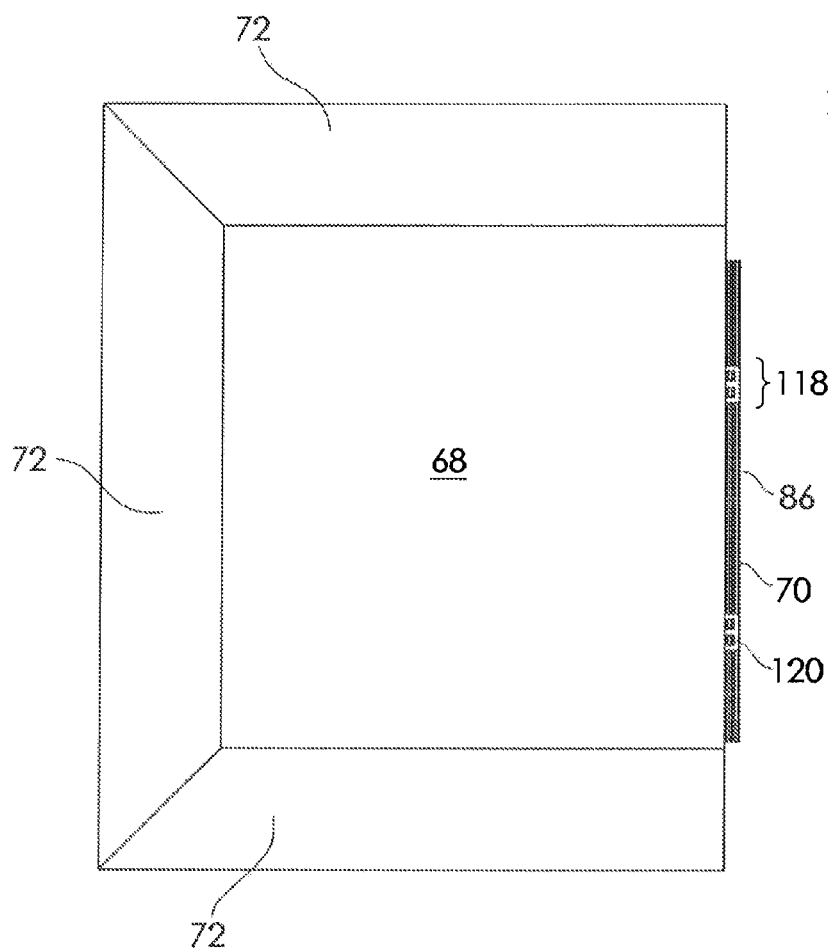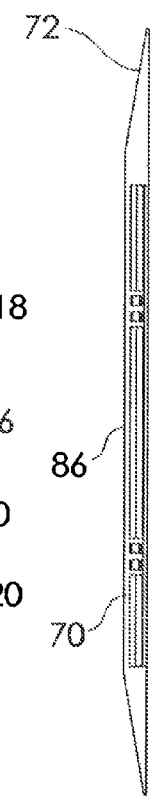
FIG. 21  FIG. 23
FIG. 22

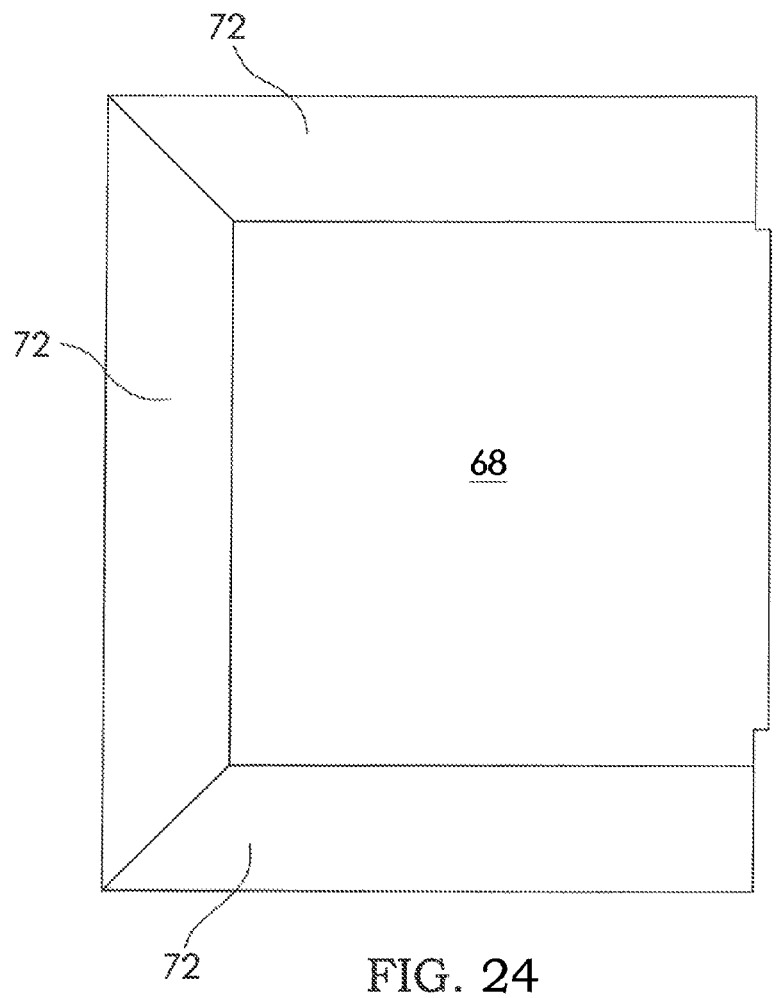
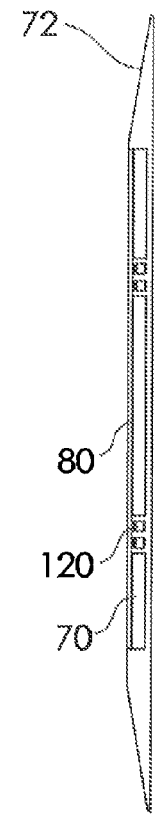
FIG. 24
FIG. 26
FIG. 25

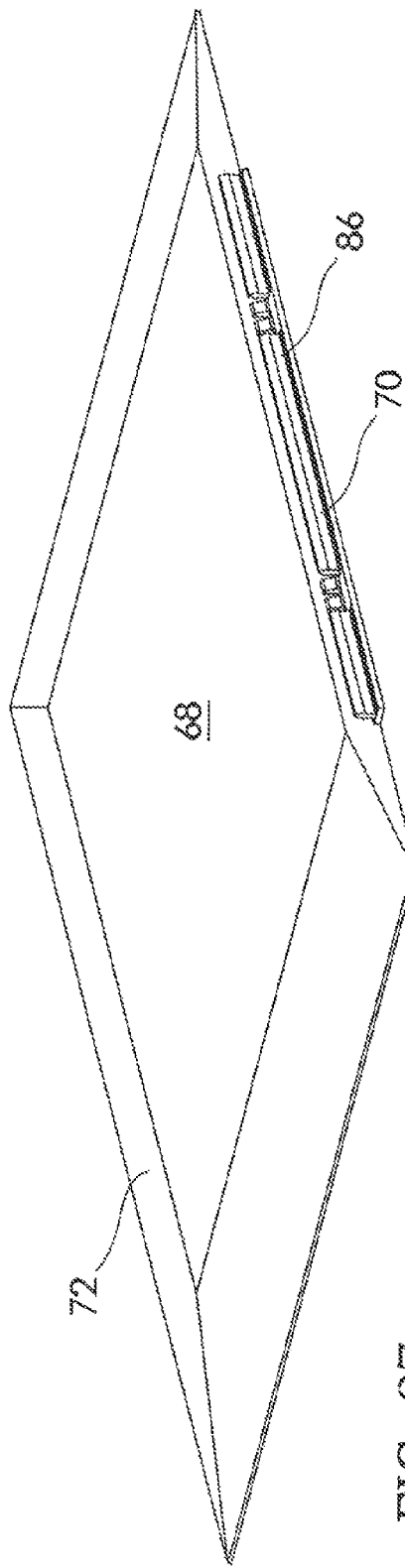
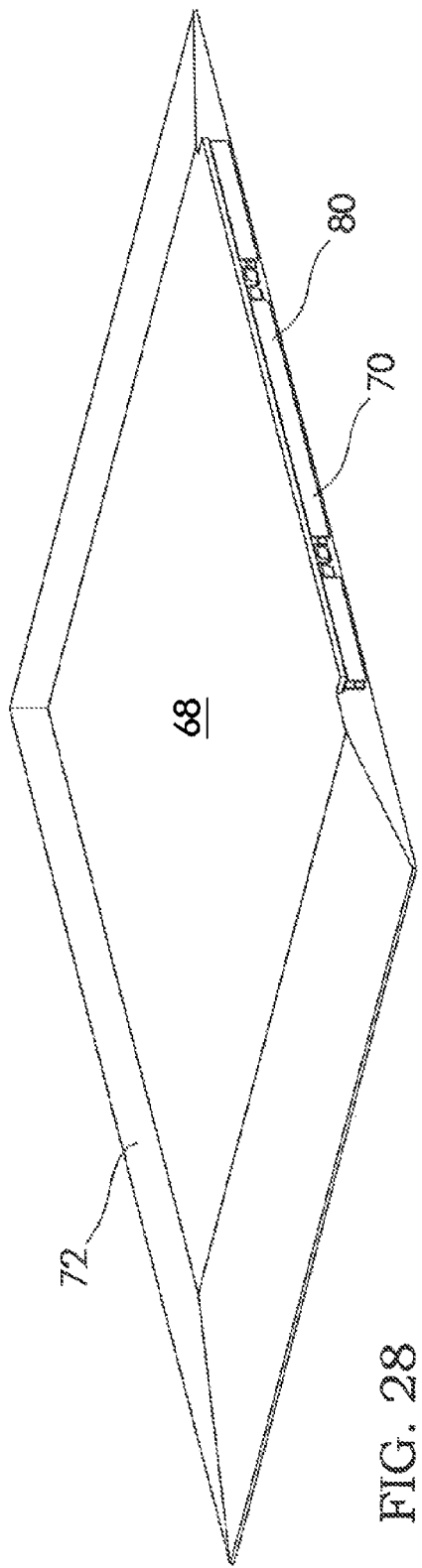

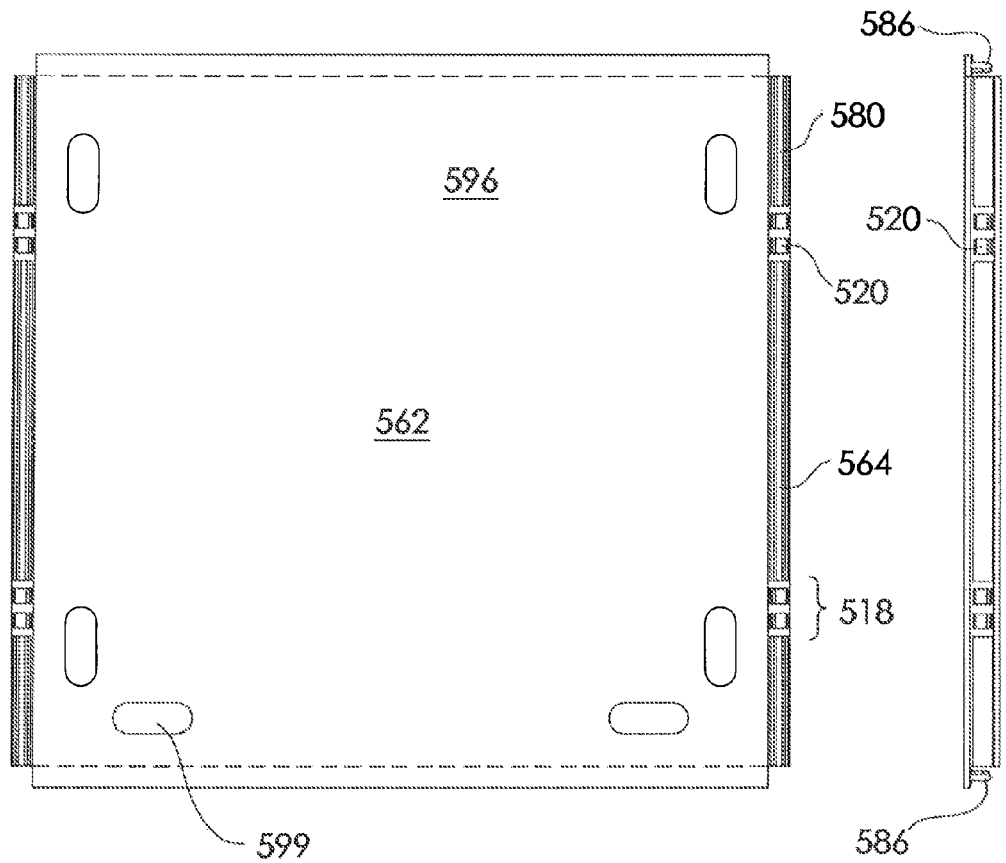
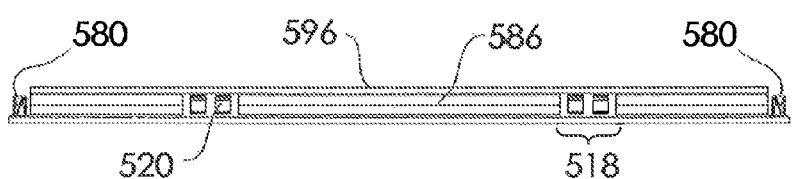
FIG. 52  FIG. 53
FIG. 54

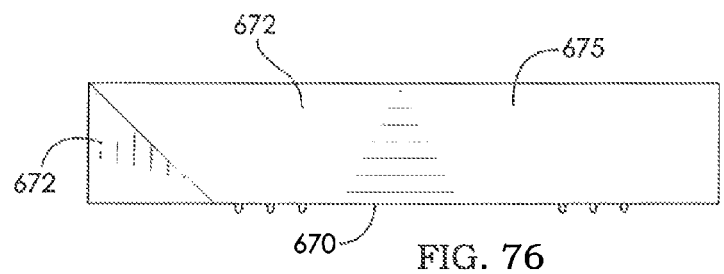 
FIG. 76  FIG. 77
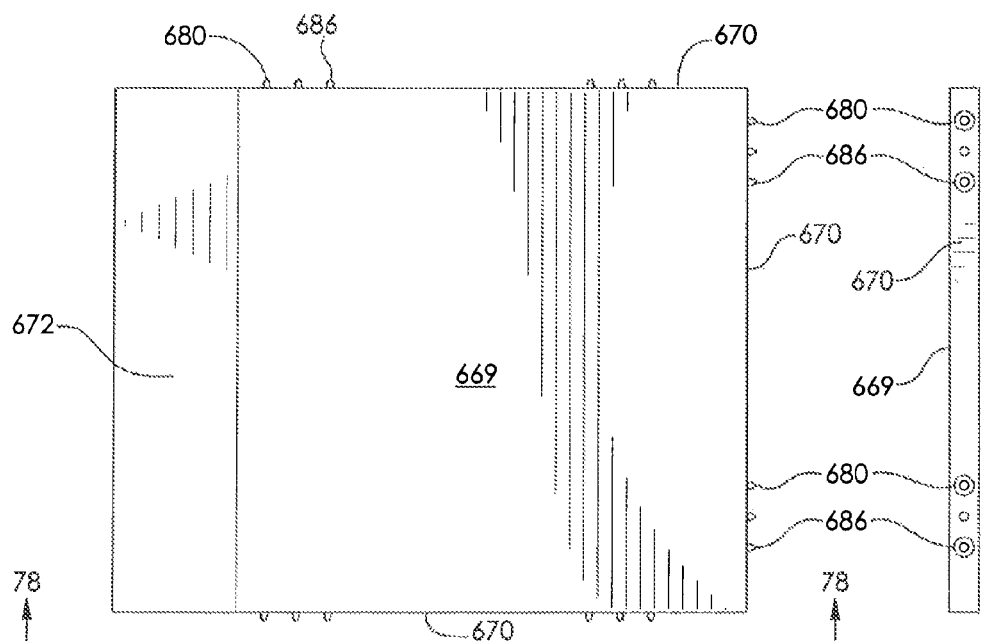
FIG. 72  FIG. 73
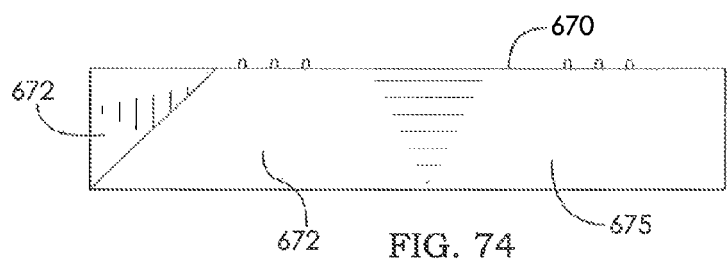 
FIG. 74  FIG. 75
FIG. 78

MODULAR INSTRUMENTED FLOOR COVERING

INCORPORATION BY REFERENCE

This application is a continuation-in-part of U.S. patent application Ser. No. 14/318,035, filed on Jun. 27, 2014, and entitled, "Modular Instrumented Floor Covering," and incorporated in its entirety for the teachings therein. Benefit of the priority filing date of Jun. 27, 2014 is hereby claimed. U.S. Pat. No. 5,952,585, issued Sep. 14, 1999, entitled "Portable Pressure Sensing Apparatus For Measuring Dynamic Gait Analysis And Method Of Manufacture," is incorporated in its entirety for the teachings therein.

TECHNICAL FIELD

The presently disclosed technologies are directed to an apparatus and method for a pressure sensitive instrumented floor, and in particular, a plurality of modular, interlocking, instrumented panels that fit together selectively, over which subjects walk for data collection.

BACKGROUND

The collection of data for subjects walking upon a floor is accomplished by laying out a pressure sensitive instrument panel. The subject walks along the panel, and data is communicated to a computer by hard wiring. This is routinely used for analyzing the gait of humans or animals. The apparatus is an over ground system using a long pressure sensor matrix laid under a carpeted walkway, which in recent years has proven to be highly accurate and easy to use in both research and clinical practice.

Such a pressure sensitive instrument panel can be used for medical and veterinary diagnosis of walking problems. It can also be used for security, to determine in real time where a subject is and in what direction the subject is moving within the space.

An exemplary pressure sensor matrix is found in U.S. Pat. No. 5,952,585, the disclosure of which is incorporated herein by reference. This patent is the basis of a product entitled, "GAITRITE®," which a 2 foot wide portable walkway system with a maximum length of 26 feet. The Gaitrite apparatus is the Gold Standard in the evaluation of Pressure based Temporal/Spatial gait analysis worldwide. The Gaitrite apparatus nevertheless has limitations, including width and length restrictions. Furthermore, the system had to be directly connected to a computer via cable. This limits the ability to walk in other than a straight line or a confined U turn. Over the years many systems have attempted and failed to provide more open walking surface or easy connectivity. All these systems to date have been too restrictive in ease of installation and in flexibility of layout options. One problem has been laying down custom pathways along which the subject can walk. The pathway selections are very limited, and cannot be changed. Another problem has been wiring the pressure sensor matrix for signal and power. These systems require custom wiring under the sensors.

There is a need, therefore, for a pressure sensitive walkway for data collection which does not require any custom hard wiring.

There is a further need for a pressure sensitive walkway for data collection as described, and that has pathways that can be reconfigured selectively.

There is a yet further need for a pressure sensitive walkway for data collection as described, and that can be installed by one person with limited skills and no tools.

There is a still further need for a pressure sensitive walkway for data collection as described, and that can be monitored locally or remotely.

SUMMARY

In one aspect, a modular instrumented floor covering assembly is used in connection with a subject walking across the assembly, a power source, and a computer. The floor covering assembly comprises a plurality of sensor panels having interlocking edges. The sensor panels are adapted for interlocking the adjacent panels together along the edges. Each sensor panel has a pressure sensor matrix responsive to a weight of the subject for generating data relating to movement of the subject. The plurality of sensor panels is adapted for selective and releasable assembly in patterns. Communicating means is provided for communicating data from the sensor panels. Power means is provided for supplying power to the sensor panels and between adjacent sensor panels.

These and other aspects, objectives, features, and advantages of the disclosed technologies will become apparent from the following detailed description of illustrative embodiments thereof, which is to be read in connection with the accompanying drawings.

BRIEF DESCRIPTION OF THE DRAWINGS

FIG. 4 is a bottom plan view of the modular instrumented panel of FIG. 1.

FIG. 5 is a left side view of the modular instrumented panel of FIG. 1.

FIG. 6 is a front elevational view of the modular instrumented panel of FIG. 1.

FIG. 13 is a top plan view of an edge panel for use with the modular instrumented panel of FIG. 1.

FIG. 14 is an end view of the edge panel of FIG. 13.

FIG. 15 is an edge view of the edge panel of FIG. 13.

FIG. 19 is a perspective view of the edge panel of FIG. 13.

FIG. 20 is a perspective view of the edge panel of FIG. 16.

FIG. 21 is a top plan view of an inert panel for use with the modular instrumented panel of FIG. 1.

FIG. 22 is an end view of the inert panel of FIG. 21.

FIG. 23 is an edge view of the inert panel of FIG. 21.

FIG. 24 is a top plan view of another inert panel for use with the modular instrumented panel of FIG. 1.

FIG. 25 is an end view of the inert panel of FIG. 24.

FIG. 26 is an edge view of the inert panel of FIG. 24.

FIG. 27 is a perspective view of the inert panel of FIG. 21.

FIG. 28 is a perspective view of the inert panel of FIG. 24.

FIG. 52 is a bottom plan view of the modular instrumented panel of FIG. 49.

FIG. 53 is a right side view of the modular instrumented panel of FIG. 49.

FIG. 54 is a rear inverted elevational view of the modular instrumented panel of FIG. 49.

Figure 59:
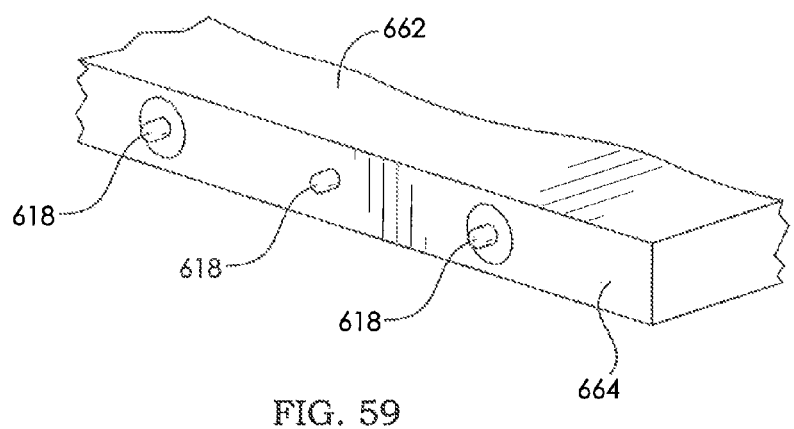
FIG. 59 is a perspective contracted assembly view of the modular instrumented panel of FIG. 55, taken at a typical corner.
Figure 60:
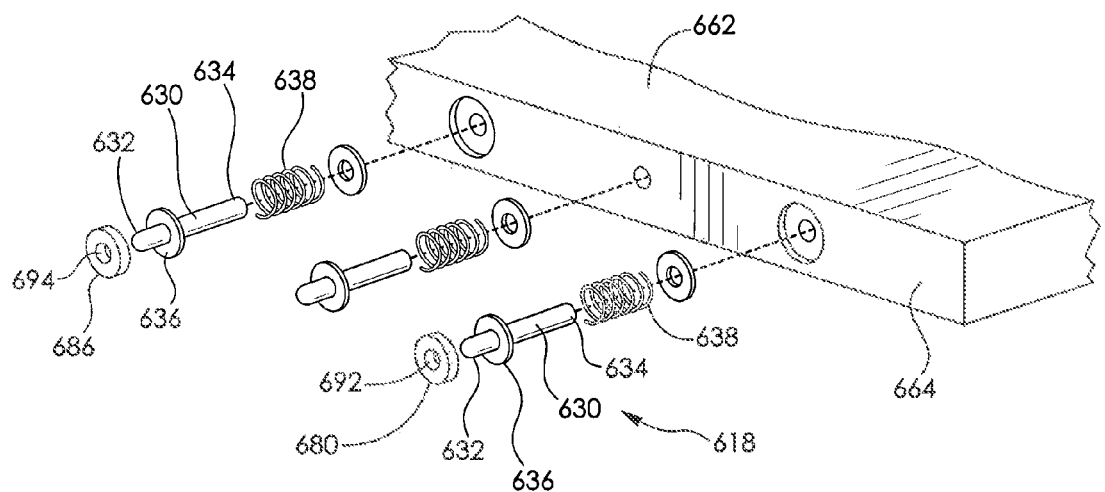

60 is a perspective exploded assembly view of FIG. 59, showing the electrical connectors and magnets.

Figures 55, 56A, 56B:
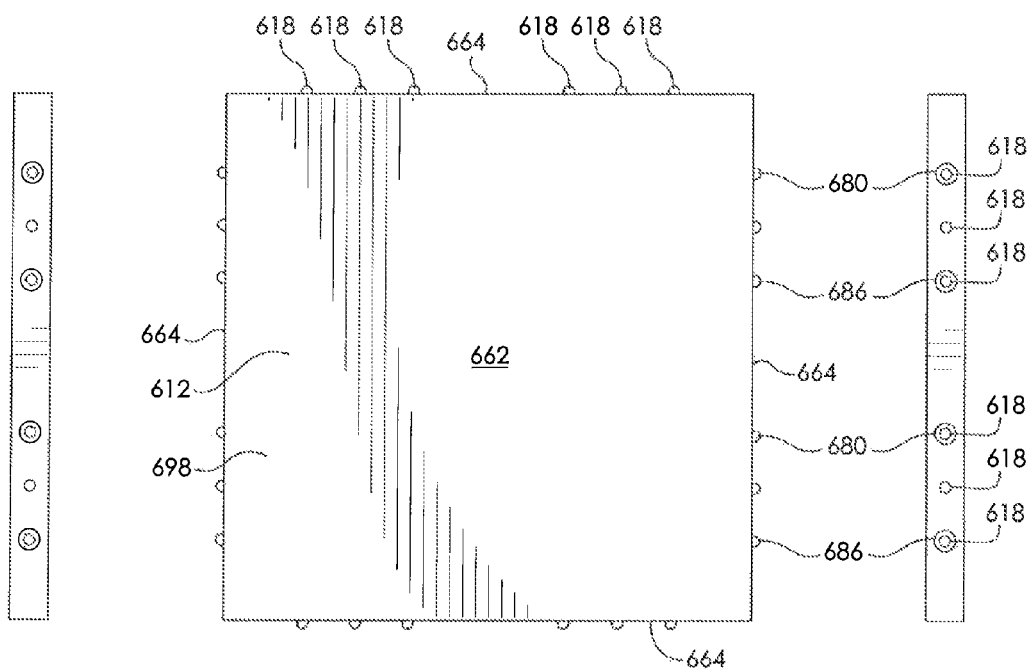
FIG. 55 is a top plan view of another modular instrumented floor covering panel constructed in accordance with the invention.
FIG. 56A is a right side view of the modular instrumented panel of FIG. 55.
FIG. 56B is a left side view of the modular instrumented panel of FIG. 55.
Figure 57A:
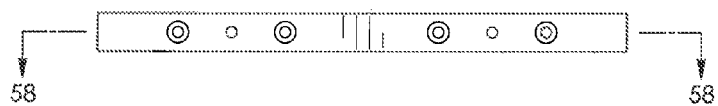
FIG. 57A is a front elevational view of the modular instrumented panel of FIG. 55.
Figure 58:
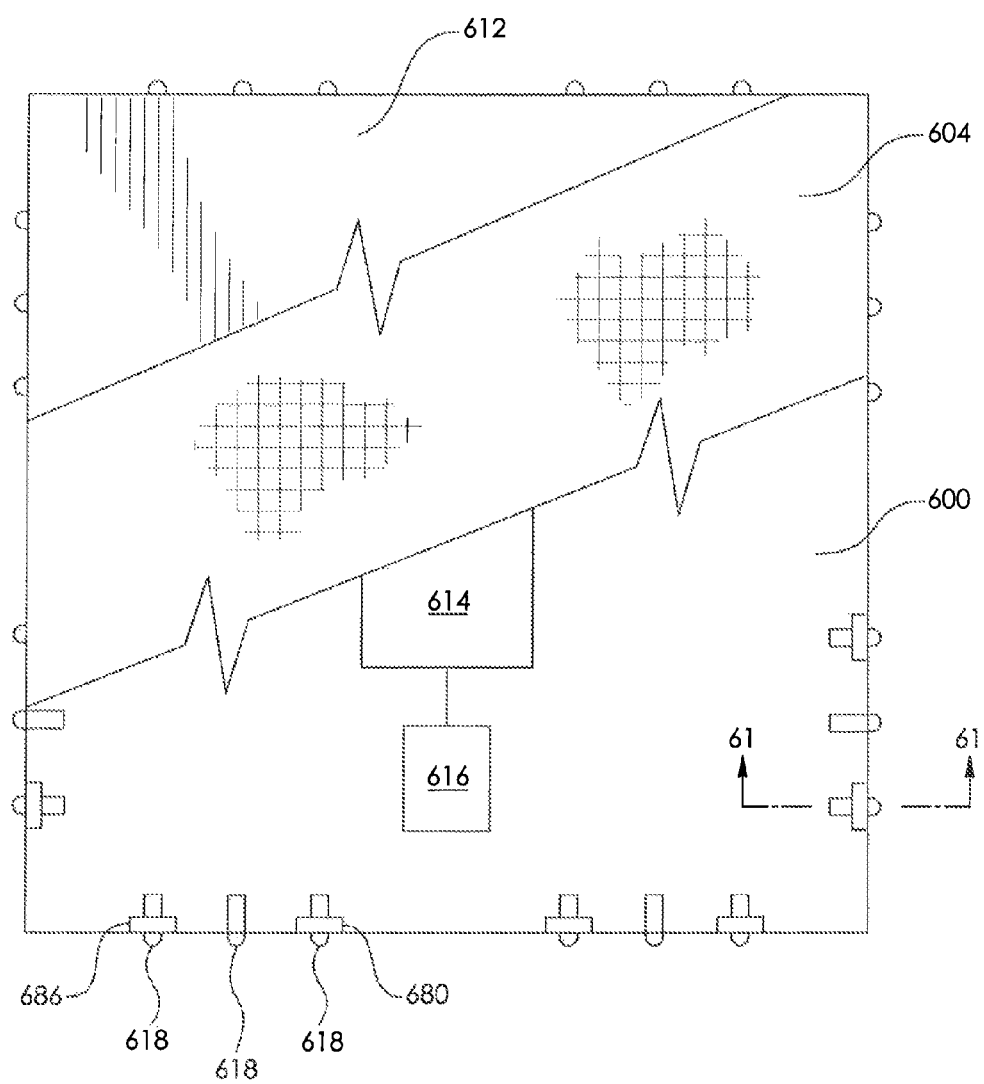
FIG. 58 is a cutaway top plan view of the modular instrumented panel of FIG. 55, taken along lines 58-58 of FIG. 57A, and showing the layers.
Figure 61:
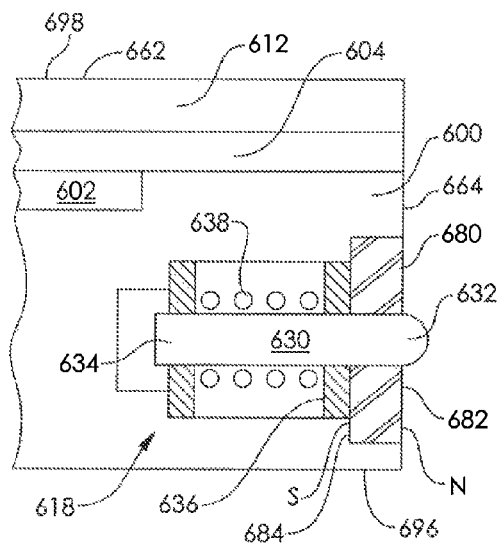

FIG. 61 is a cross-sectional elevational detail view of the modular instrumented panel assembly of FIG. 55, taken along lines 61-61 of FIG. 58, and showing the magnet and electrical connector of a typical sensor panel.

Figure 62:
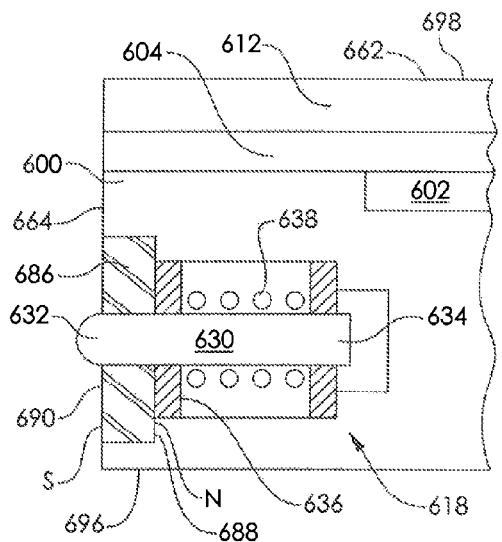

FIG. 62 is a cross-sectional elevational detail view of an adjacent panel assembly, and showing the magnet and electrical connector of the adjacent sensor panel.

Figure 63:
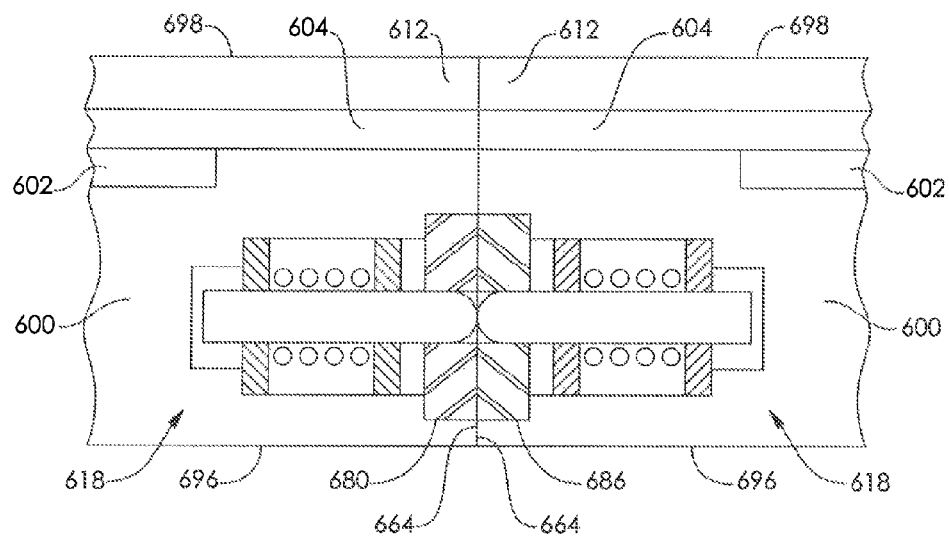

FIG. 63 is a cross-sectional elevational detail view of the sensor panels of FIGS. 61 and 62, showing the interlocking panels assembled together.

Figure 57B:
FIG. 57B is a rear elevational view of the modular instrumented panel of FIG. 55.
Figure 64:
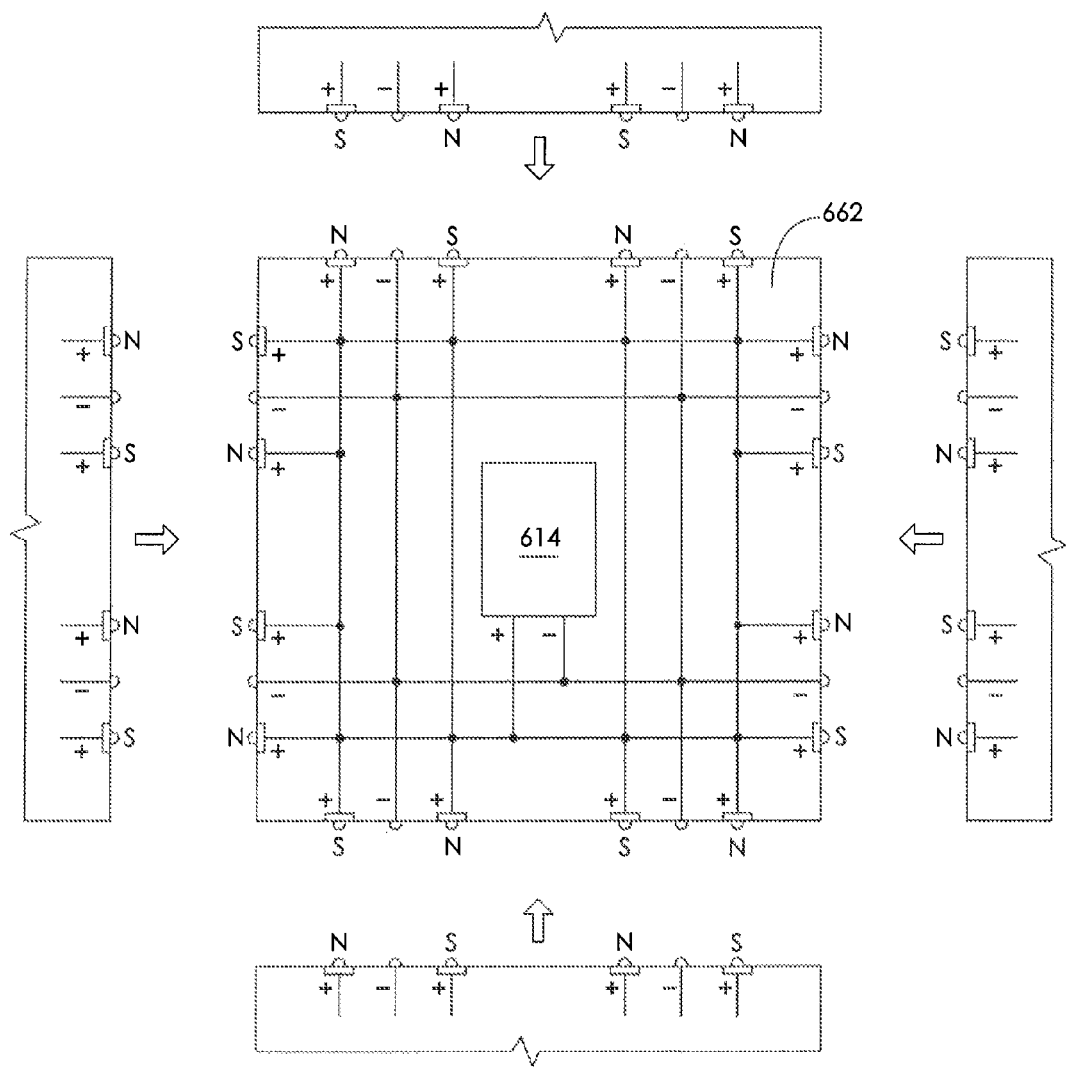

FIG. 64 is a cutaway top plan view of the modular instrumented panel of FIG. 55, taken along lines 58-58 of FIG. 57F, and showing the power connections in the panel.

Figures 65, 67:
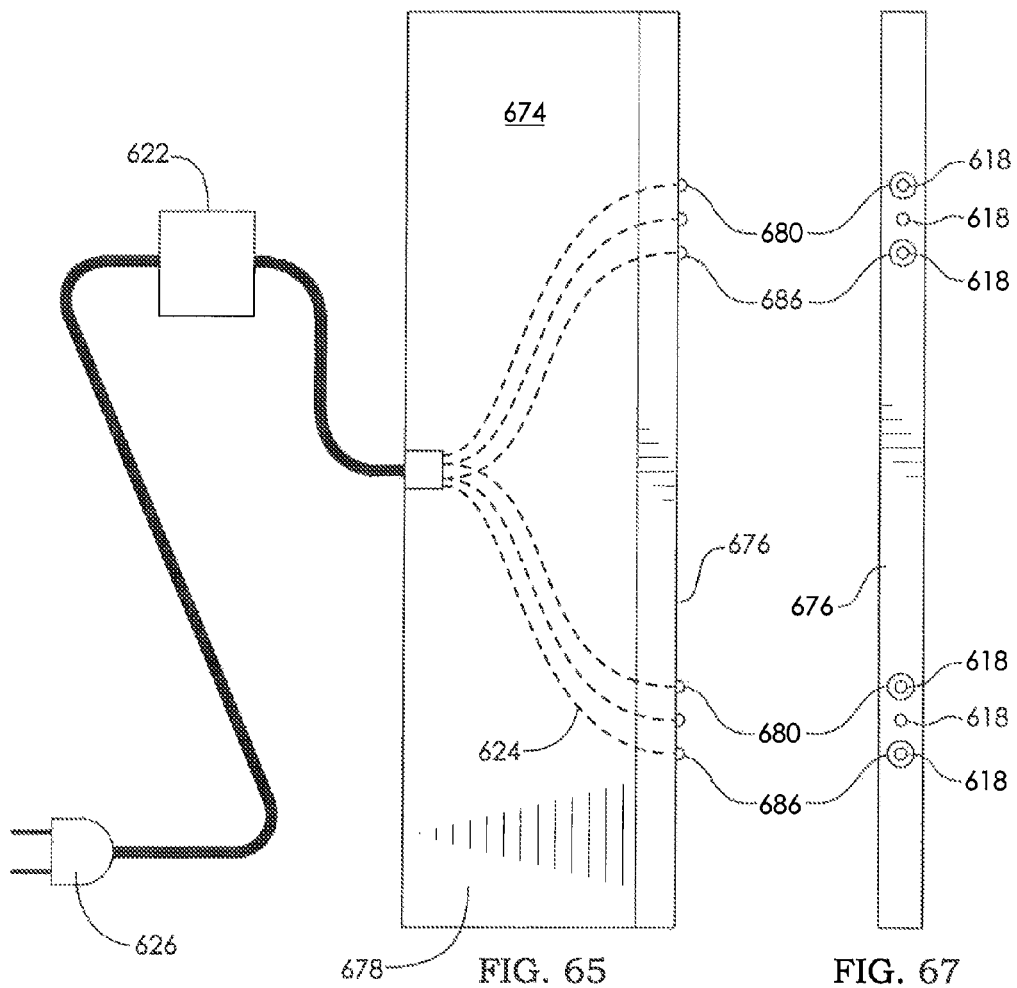

FIG. 65 is a top plan view of an edge panel for use with the modular instrumented panel of FIG. 55.

Figure 66:
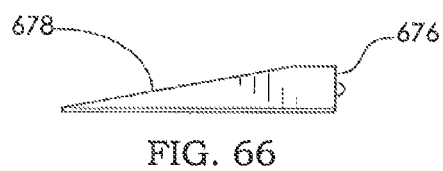

FIG. 66 is an end view of the edge panel of FIG. 65.

FIG. 67 is an edge view of the edge panel of FIG. 65.

Figures 68, 70:
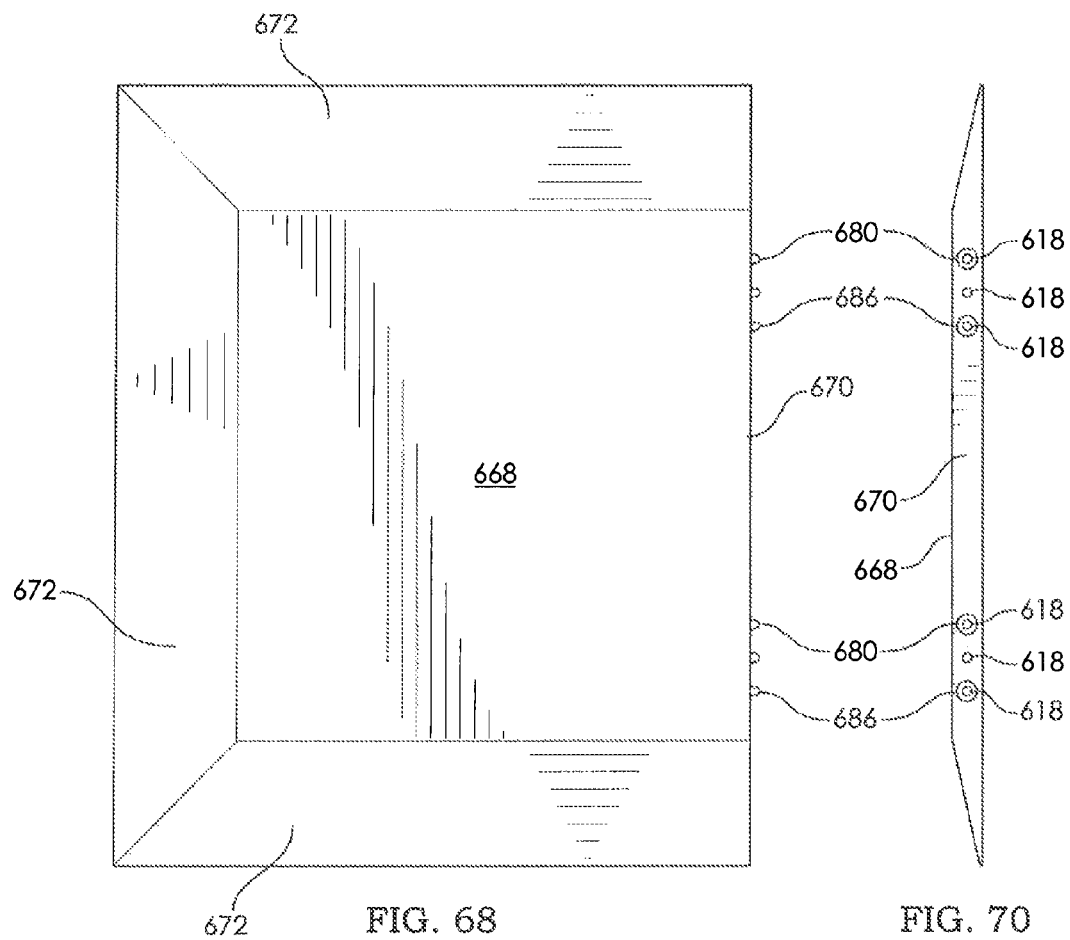

FIG. 68 is a top plan view of an inert panel for use with the modular instrumented panel of FIG. 55.

Figure 69:
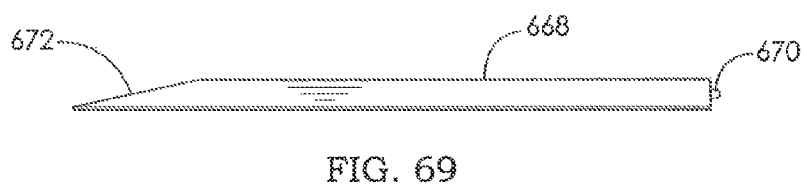

FIG. 69 is an end view of the inert panel of FIG. 68.

FIG. 70 is an edge view of the inert panel of FIG. 68.

Figure 71:
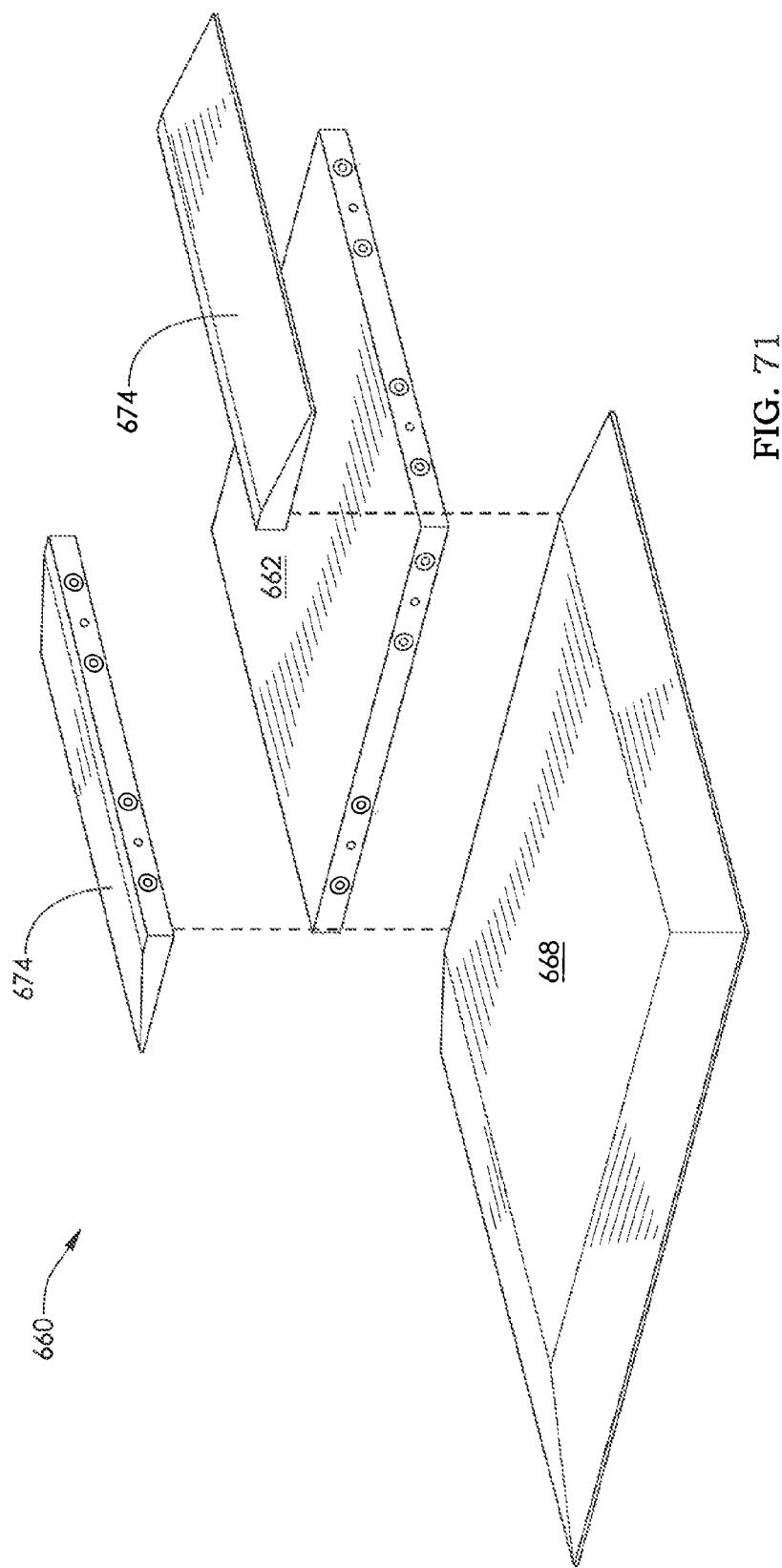

FIG. 71 is a perspective assembly exploded view of the modular instrumented panel of FIG. 55, and two edge panels of FIG. 65, and the inert panel of FIG. 68 showing the assembly procedure.

FIG. 72 is a top plan view of another inert panel for use with the modular instrumented panel of FIG. 55.

FIG. 73 is an end view of the inert panel of FIG. 72.

FIG. 74 is a top plan view of another edge panel for use with inert panel of FIG. 72.

FIG. 75 is an end view of the edge panel of FIG. 74.

FIG. 76 is a top plan view of another edge panel for use with inert panel of FIG. 72.

FIG. 77 is an end view of the edge panel of FIG. 76.

FIG. 78 is an edge view of the inert panel of FIG. 72, taken along lines 78-78 of FIG. 72.

Figure 79:
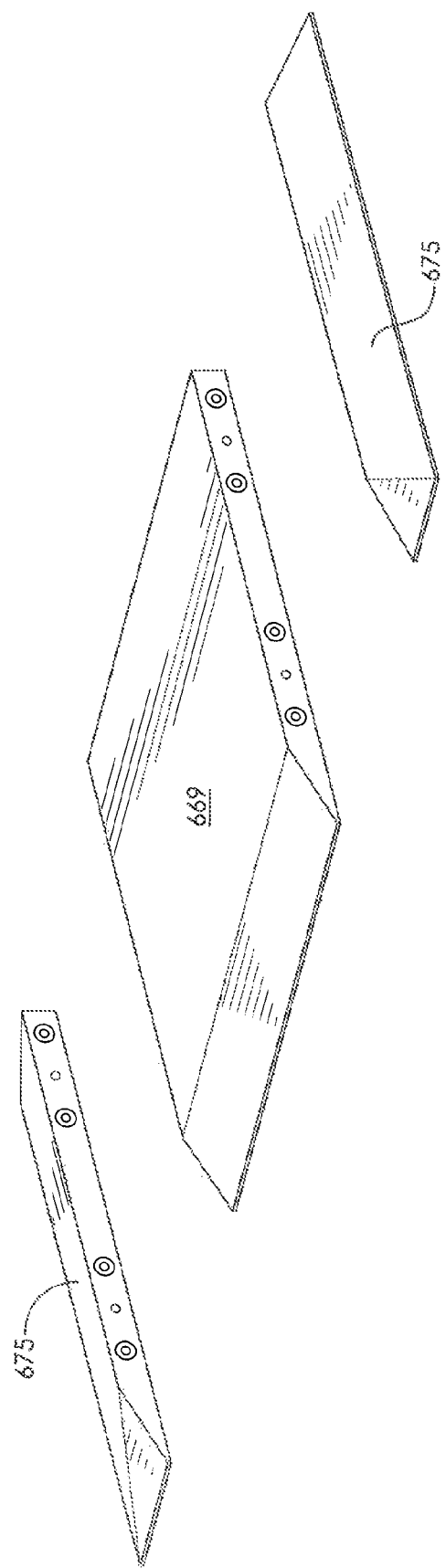

FIG. 79 is a perspective assembly exploded view of the inert panel of FIG. 72, and two edge panels of FIGS. 74 and 76, showing the assembly procedure.

Figure 80:
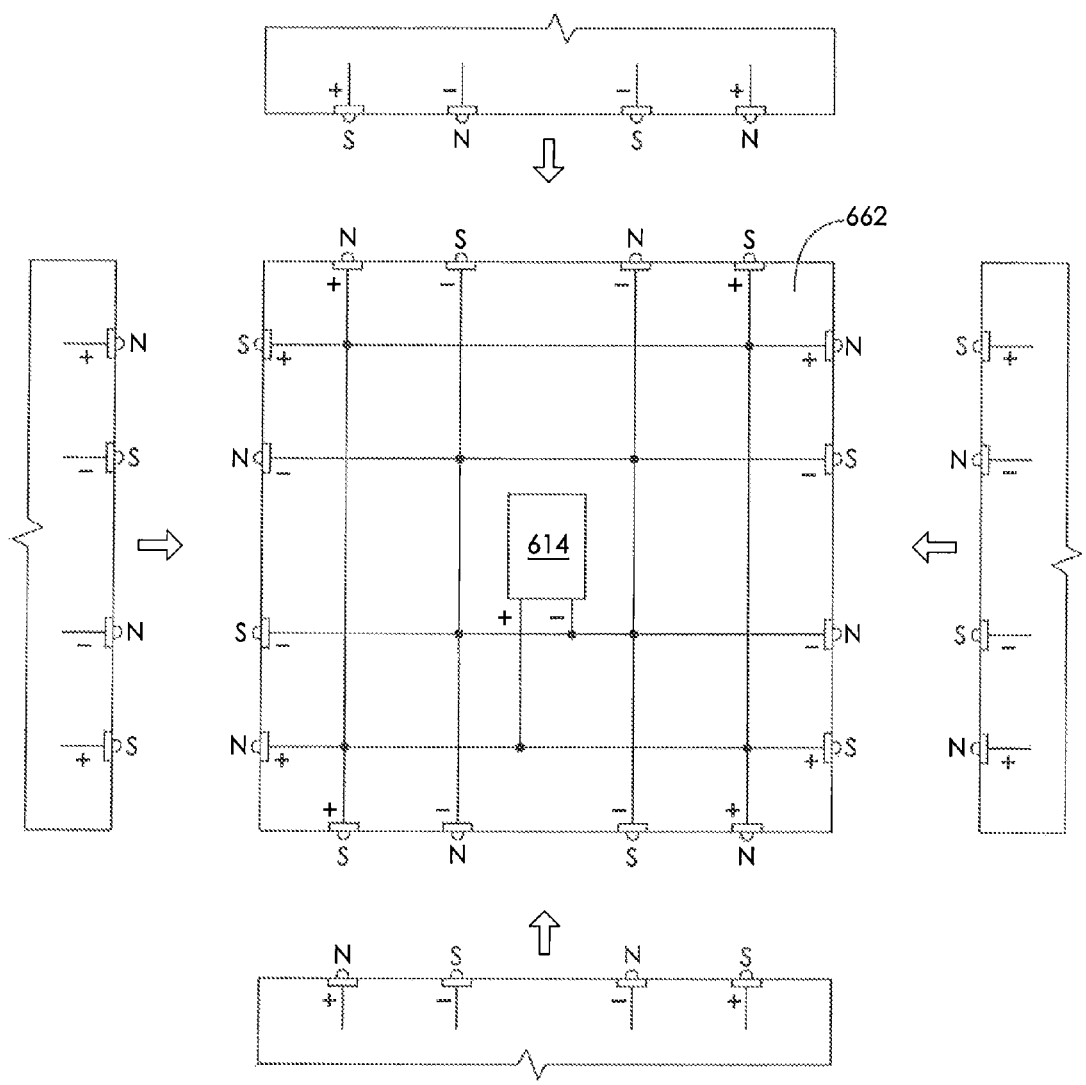

FIG. 80 is a cutaway top plan view of the modular instrumented panel of FIG. 55, taken along lines 58-58 of FIG. 57F, and showing alternate power connections in the panel.

It should be noted that the drawings herein are not to scale.

DETAILED DESCRIPTION

Describing now in further detail these exemplary embodiments with reference to the Figures as described above, a modular instrumented floor covering assembly 60 is used in connection with a subject (not shown) walking across the assembly. The floor covering assembly 60 comprises a plurality of sensor panels 62 having interlocking edges 64. The sensor panels 62 are adapted for interlocking the adjacent panels together along the edges 64. Each sensor panel 62 has a pressure sensor matrix 66 responsive to a weight of the subject for generating data relating to movement of the subject. The plurality of sensor panels 62 is adapted for selective and releasable assembly in patterns, as shown in FIGS. 39-44. The patterns shown can be assembled in combinations as needed. Thus, any pattern of connected square elements can be created. The panels must be laid out in uniform orientation, not rotated with respect to one another. Communicating means 114 116 is provided for communicating data between adjacent sensor panels and from the sensor panels to an outside computer (not shown).

At least one inert panel 68 is provided, having one interlocking edge 70. The inert panel 68 is adapted for interlocking with one of the sensor panels 62 along the interlocking edge 70. The inert panel 68 has a beveled edge 72 along remaining edges so as to preclude tripping the subject. The inert panel 68 is for guiding the subject toward the sensor panels 62. The subject will take one or two steps on the inert panel 68 before stepping onto the sensor panels 62, to ensure a uniform gait.

At least one edge panel 74 is provided, having one interlocking edge 76. Typically, two edge panels 74, one on each side, will accompany each sensor panel 62 along the entire pattern. This will give the system a finished, non-trip edge. Furthermore, power can be connected to an edge panel 74 anywhere along the entire pattern, as will be explained hereinbelow. The edge panel 74 is adapted for interlocking with one of the sensor panels 62 along the interlocking edge 76. The edge panel 74 has a beveled edge 78 opposing the interlocking edge 76 so as to preclude tripping the subject.

The interlocking edges 64, 70, and 76 each include a channel 80 extending along at least one edge, and in particular, along two edges 64 of each sensor panel 62. The channel, typically an elongated channel strip 80, also extends along one edge 70 of the inert panel 68, and along one edge 76 of the edge panel 74. The channel strip 80 has a U-shaped cross-section with a tapered opening 82 and at least one inside shoulder 84.

An arrow 86 extends along at least one edge, and in particular, along two edges 64 of each sensor panel 62. The arrow, typically an elongated arrow strip 86, also extends along one edge 70 of the inert panel 68, and along one edge 76 of the edge panel 74. The arrow strip 86 has an arrowhead-shaped cross-section with a tapered outer portion 88 and at least one outside shoulder 90. The arrow strip 86 of each panel is releasably inserted into the channel strip 80 of the adjacent panel for interlocking the adjacent panels together. The arrow strip outside shoulder 90 releasably engages the channel strip inside shoulder 84 so as to resist disengaging, as shown in FIGS. 31-34.

The channel strip 80 has an assembly direction 92 defined as facing the opposed arrow strip 86. The arrow strip 86 has an assembly direction 94 defined as facing the opposed channel strip 80.

Each sensor panel 62 defines a polygon having four edges. In the preferred embodiment, each sensor panel 62 defines a square. The elongated channel strip 80 extends along two edges of each sensor panel 62. The elongated arrow strip 86 extends along the remaining two edges of each sensor panel 62.

In the preferred embodiment, the elongated channel strip 80 extends along two adjacent edges of each sensor panel 62. The elongated arrow strip 86 extends along the remaining two adjacent edges of each sensor panel 62.

Each sensor panel 62 includes a generally planar bottom surface 96 and an opposed top surface 98 generally parallel to the bottom surface 96. The channel strip 80 faces away from either the bottom surface or the top surface. In the preferred embodiment, the channel strip 80 extends downward in the assembly direction 92, away from the frame layer 106, and generally perpendicular to the top surface 98. The arrow strip 86 faces away from the opposed one of either the bottom surface 96 or the top surface. In the preferred embodiment, the arrow strip 86 extends upward in the assembly direction 94, away from the base layer 100, and generally perpendicular to the bottom surface 96. The panels are assembled by pressing each panel downward in a generally vertical direction. Handholes 99 are provided in the bottom surface 96.

Each sensor panel 62 includes a generally rigid base layer 100 extending upward from the bottom surface 96. A circuit layer 102 extends upward from the base layer 100. A sensor matrix layer 104 extends upward from the circuit layer 102.

A frame layer 106 extends upward from the sensor matrix layer 104. The frame layer 106 extends perimetrically around the sensor panel 62. The frame layer 106 has an interior space 108. A fill layer 110 extends upward from the sensor matrix layer 104 coextensive with the frame layer 106. The fill layer 110 is composed of flexible material, and is disposed within the frame layer interior space 108.

A cover layer 112 extends upward from the frame layer 106 to the top surface 98. The cover layer 112 is composed of flexible material, and extends across the fill layer 110 and the frame layer 106.

The cover layer 112 and the fill layer 110 will convey the weight of the subject to the sensor matrix layer 104. The rigid or semi-rigid circuit layer 102 and base layer 100 will support the weight of the subject.

At least one circuit board 114 is immersed in the circuit layer 102. The circuit board 114 is operatively electrically connected to the sensor matrix 66 for collecting data from the sensor matrix 66.

Data from the sensor array can be sent between panels and outward from the panel assembly by hardwired means or by wireless means. A transmitter 116 is immersed in the circuit layer 102 and operatively electrically connected to the circuit board 114 for transmitting data wirelessly. The wireless transmitter 116 is typically a wireless local area network (WLAN or Wi-Fi®) transceiver, and is well known by those skilled in the art. The data is sent to an outside computer (not shown) for analysis. Individual sensor panels 62 can be repositioned easily into different patterns due to the wireless communication.

Power means 118 is provided for supplying power to the sensor panels 62 and between adjacent sensor panels 62. The power means comprises at least one pair, and preferably two pairs, of electrical connectors 118 disposed on each edge 64 of each of the sensor panels 62. One of the pair is for positive voltage, and the remaining one of the pair is for negative voltage. The connectors 118 on adjacent sensor panels 62 are operatively electrically and releasably connected together upon interlocking adjacent panels together along the edges.

At least one pair of the electrical connectors 118 is disposed on the interlocking edge 76 of the edge panel. The electrical connectors 118 are adapted for operatively electrically and releasably connecting to the electrical connectors 118 on adjacent sensor panels 62.

A power supply 122 is provided, which operatively electrically and releasably connects to the electrical connectors 118 on the edge panel 74. Additional power supplies 122 can be connected to edge panels 74 wherever convenient, and as needed. For example, a short pattern may need only one power supply 122. A more lengthy pattern requires more power, and hence, a second or third power supply 122 can be connected anywhere along the pattern.

A conductor 120 on the panel interlocking edge 64, 70, and 76 is adapted for contacting a conductor 120 on the adjacent panel interlocking edge with spring bias. Two conductors 120 comprise one electrical connector 118. Wires 124 connect the power supply 122 to the electrical connectors 118. A plug 126 connects the power supply 122 to an electrical source (not shown).

Figure 3:
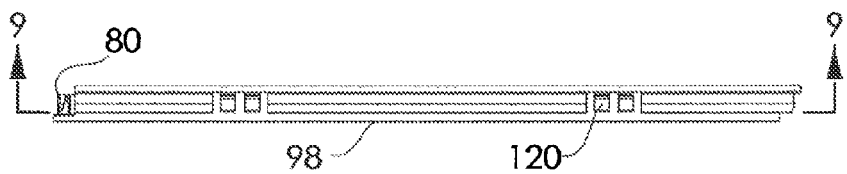
FIG. 3 is an inverted rear elevational view of the modular instrumented panel of FIG. 1.
Figures 1, 2:
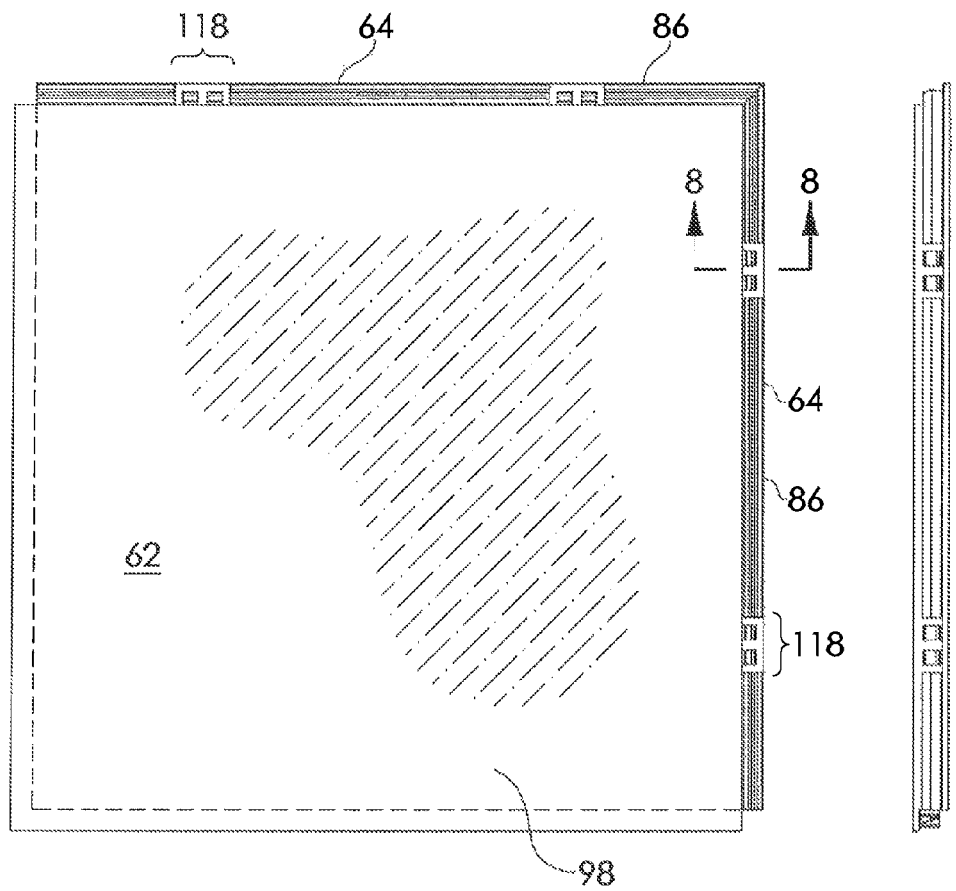
FIG. 1 is a top plan view of a modular instrumented floor covering panel constructed in accordance with the invention.
FIG. 2 is a right side view of the modular instrumented panel of FIG. 1.
Figure 7:
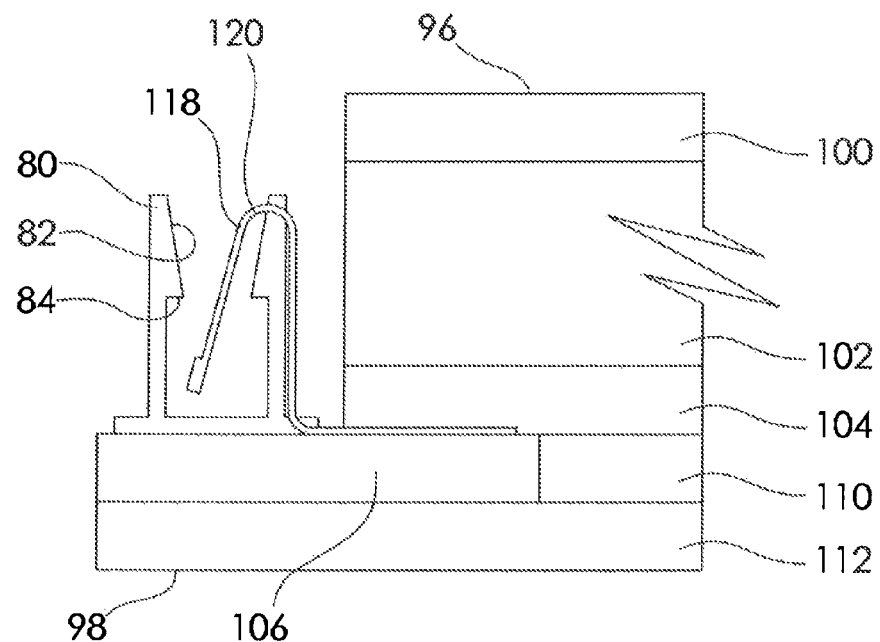
FIG. 7 is a cross-sectional elevational detail view of the modular instrumented panel of FIG. 1, taken along lines 7-7 of FIG. 4.
Figure 8:
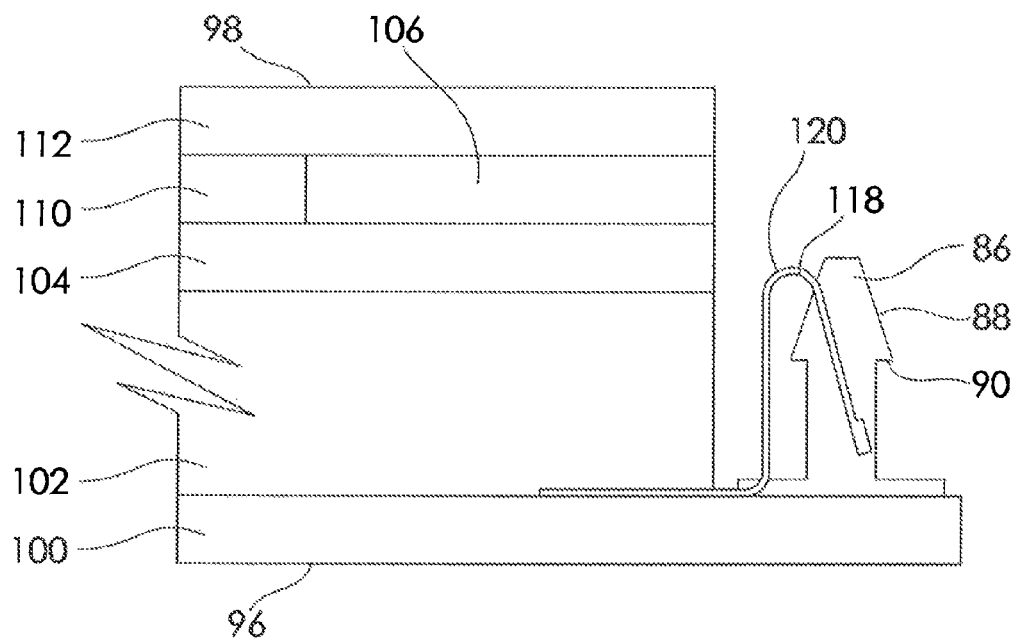
FIG. 8 is a cross-sectional elevational detail view of the modular instrumented panel of FIG. 1, taken along lines 8-8 of FIG. 1.
Figure 9A:
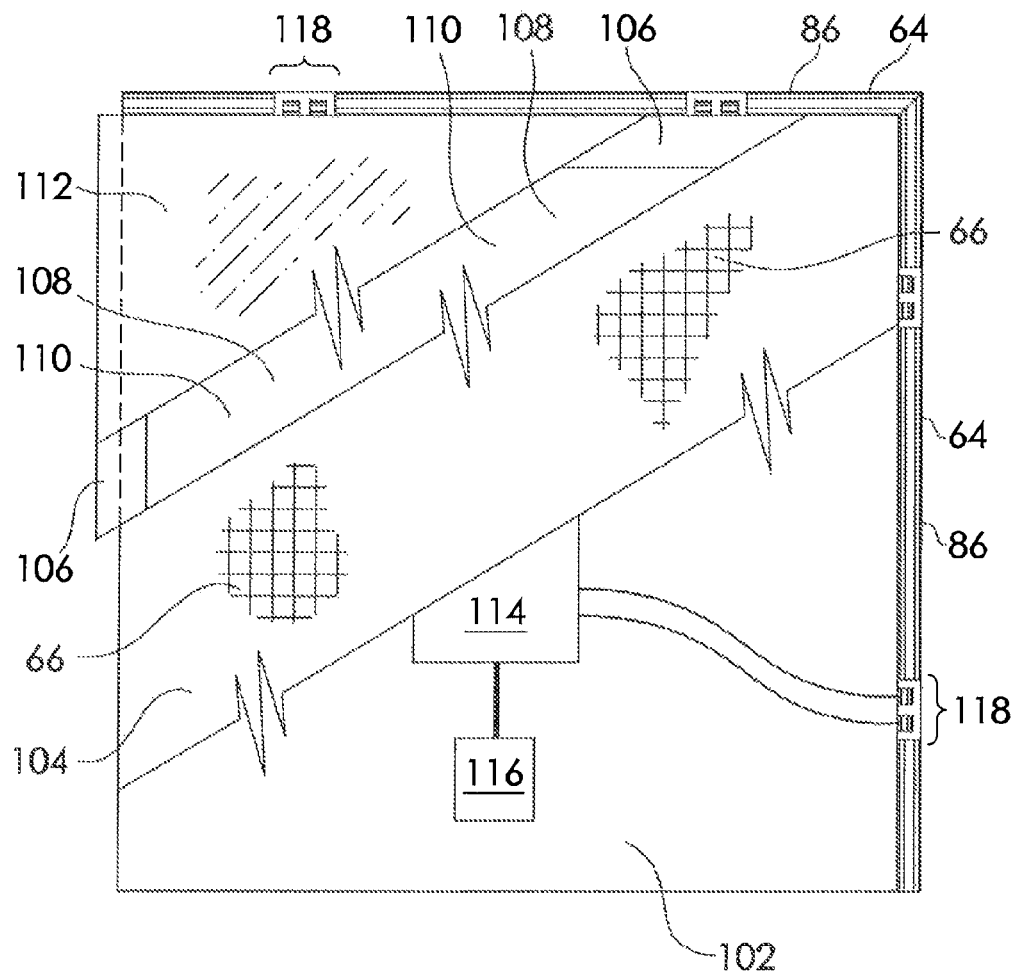
FIG. 9A is a cutaway top plan view of the modular instrumented panel of FIG. 1, taken along lines 9-9 of FIG. 3, and showing the layers.
Figure 9B:
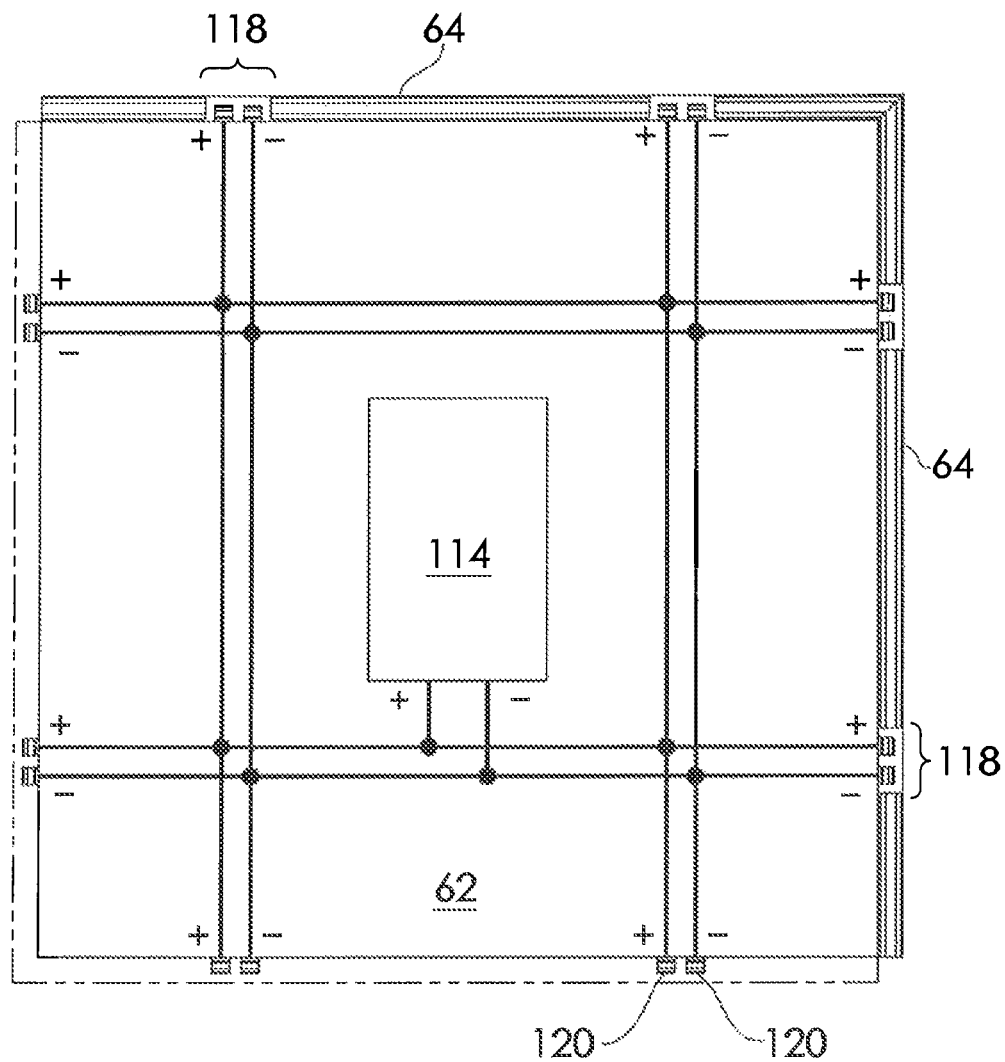
FIG. 9B is a cutaway top plan view of the modular instrumented panel of FIG. 1, taken along lines 9-9 of FIG. 3, and showing the power connections in the panel.
Figure 9C:
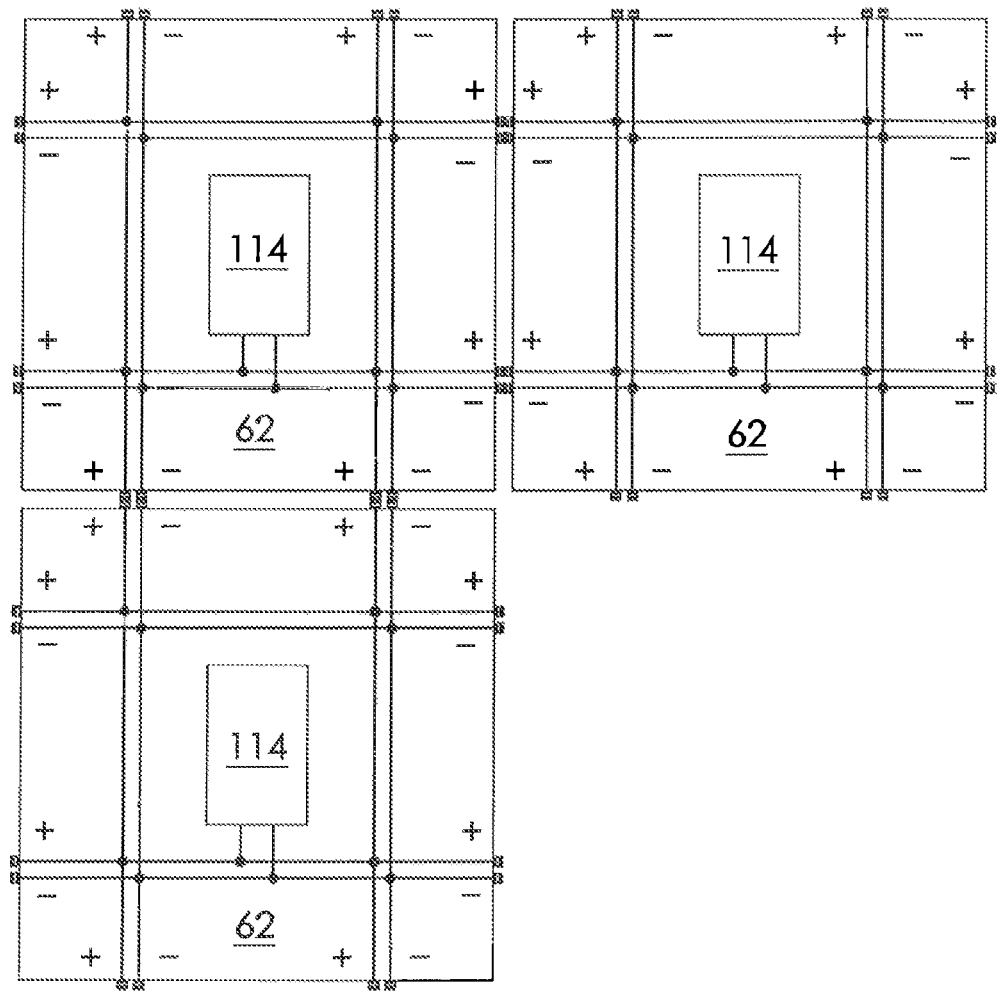
FIG. 9C is a cutaway top plan view of the modular instrumented panel of FIG. 1, taken along lines 9-9 of FIG. 3, and showing the power connections between assembled panels.
Figure 10:
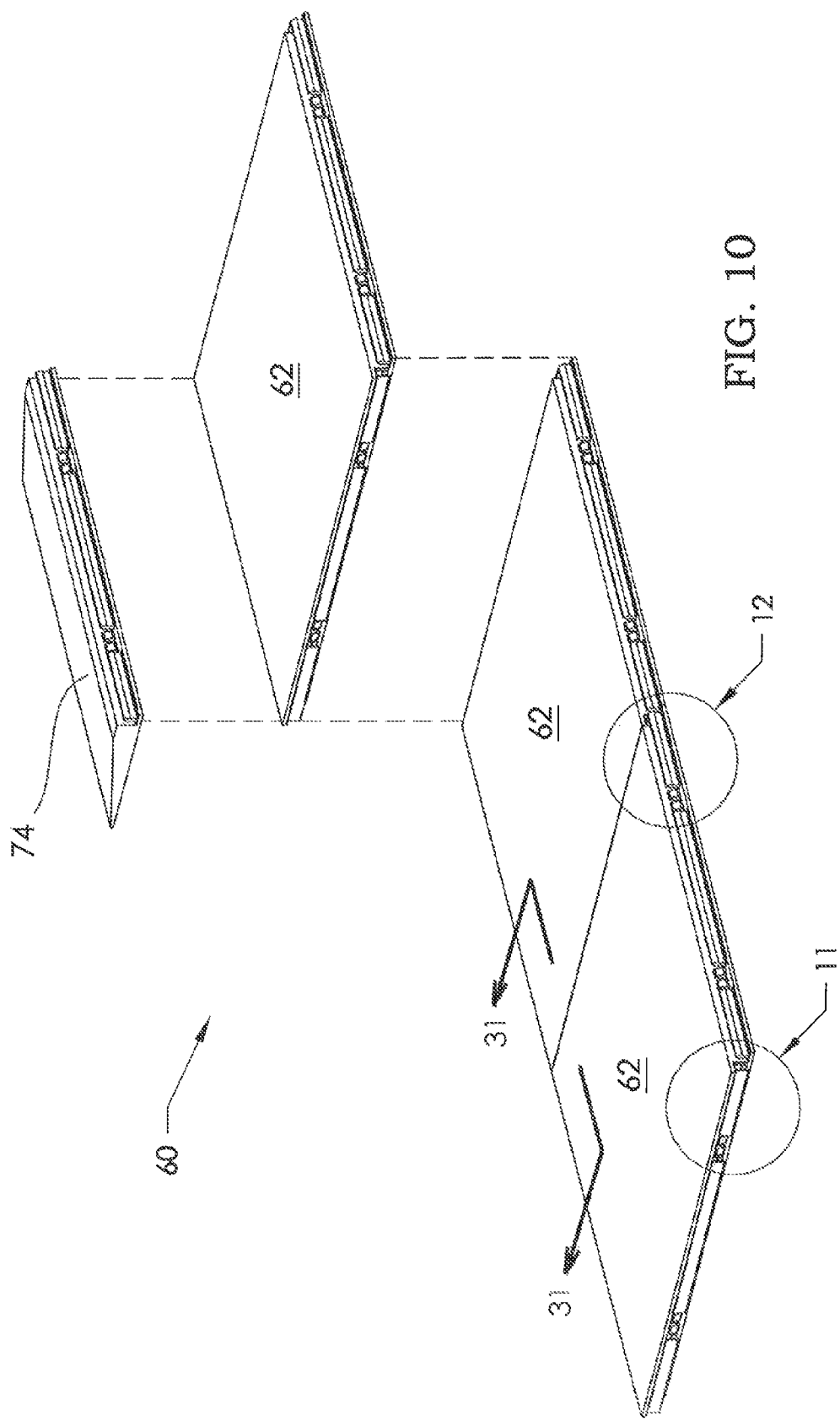
FIG. 10 is a perspective assembly view of three of the modular instrumented panels of FIG. 1, and an edge panel, showing the assembly procedure.
Figure 11:
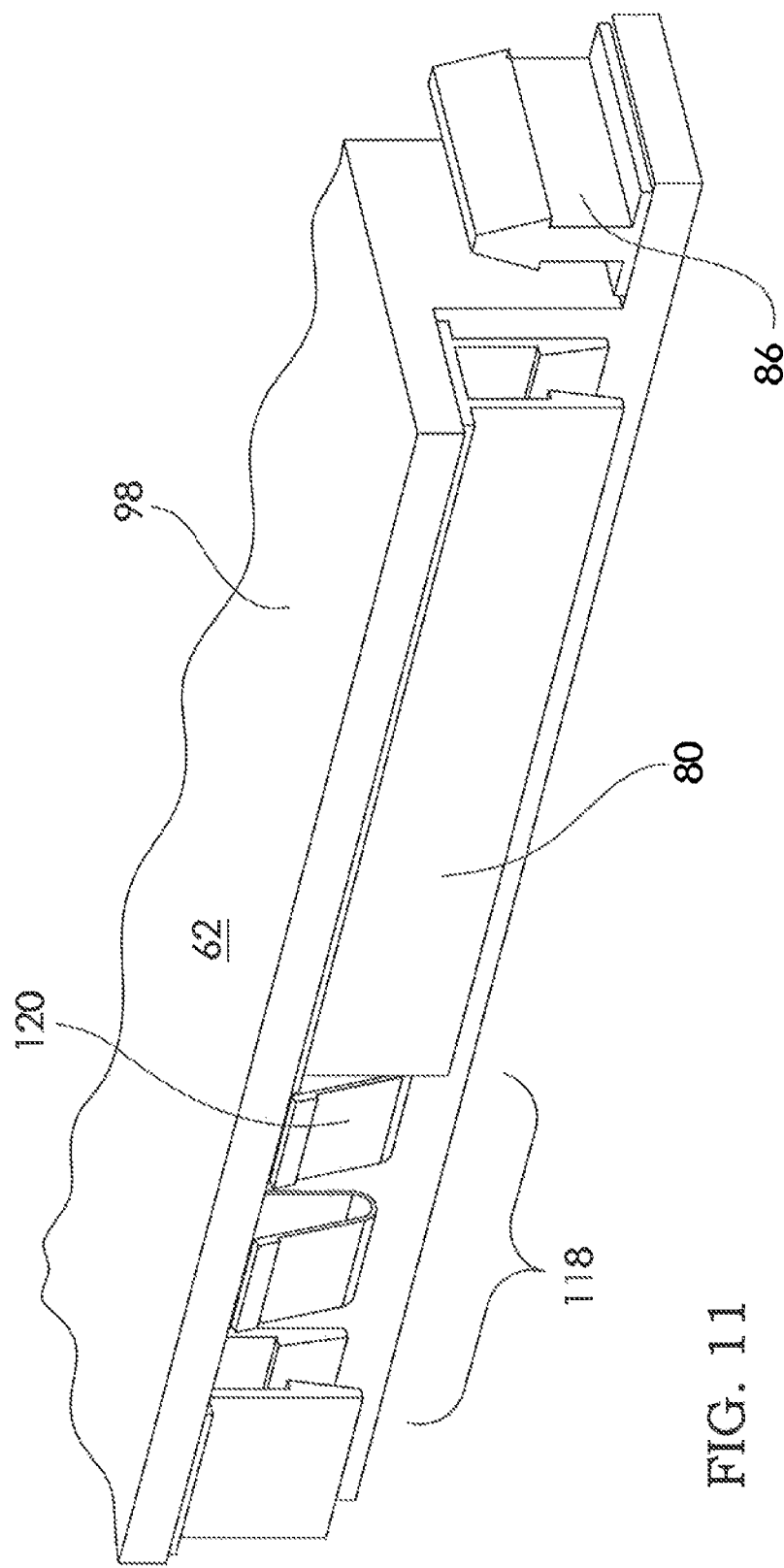
FIG. 11 is an enlarged, perspective detail view of the modular instrumented panel of FIG. 1, taken at detail 11 of FIG. 10.
Figure 12:
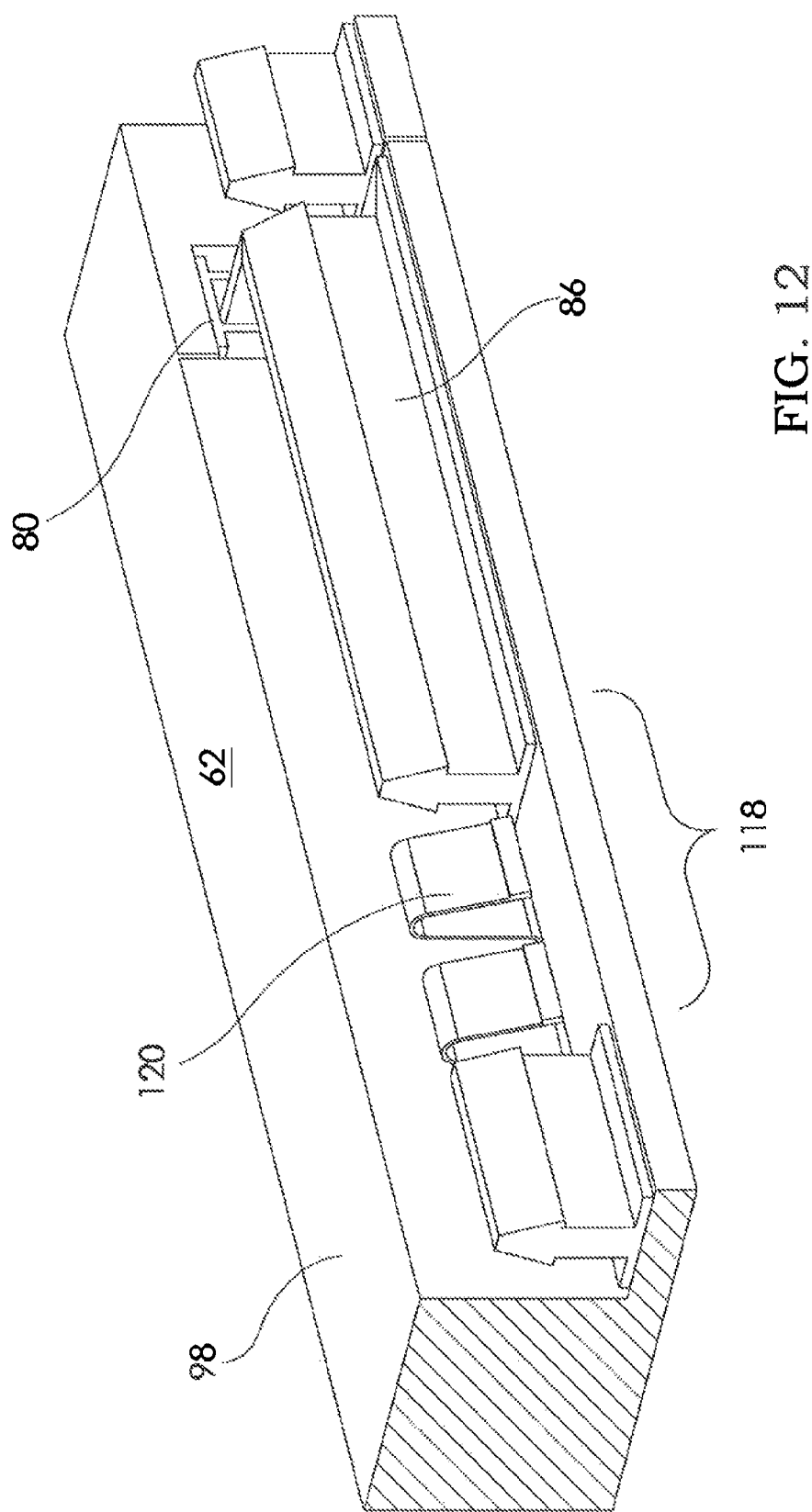
FIG. 12 is an enlarged, perspective detail view of the modular instrumented panel of FIG. 1, taken at detail 12 of FIG. 10.
Figure 17:
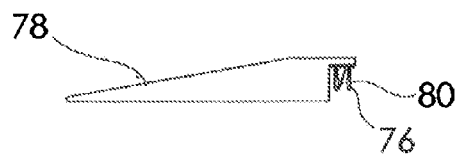
FIG. 17 is an end view of the edge panel of FIG. 16.
Figures 16, 18:
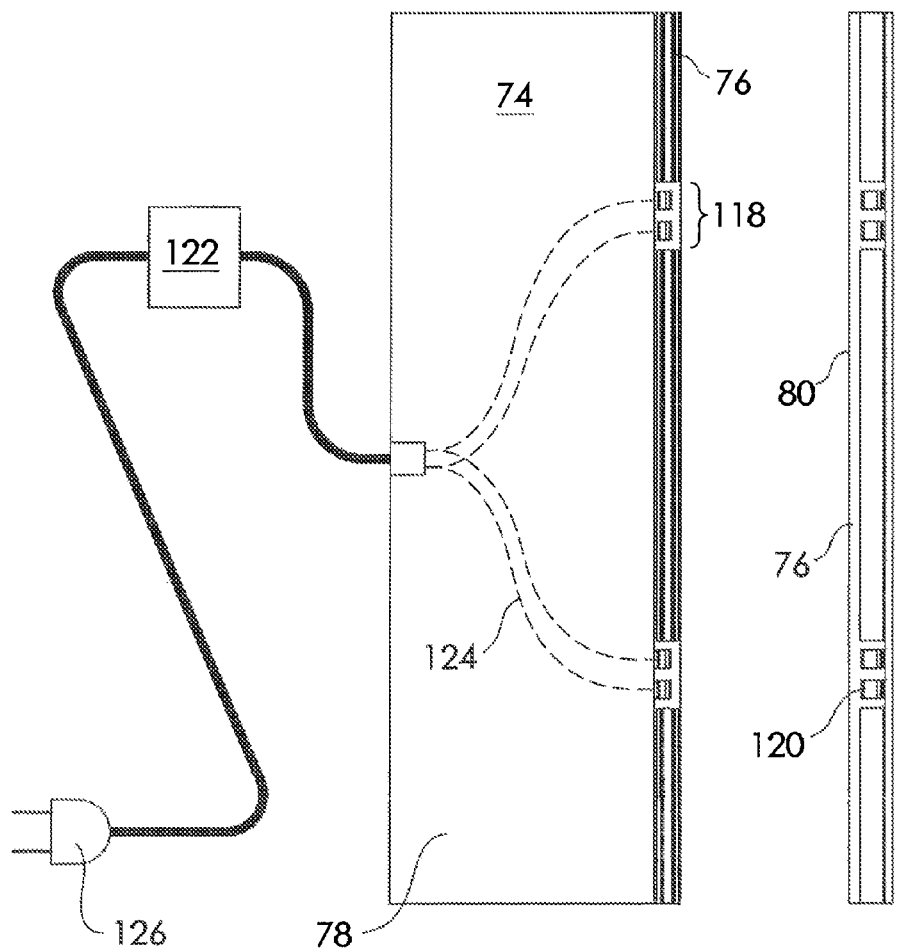
FIG. 16 is a bottom plan view of another edge panel for use with the modular instrumented panel of FIG. 1.
FIG. 18 is an edge view of the edge panel of FIG. 16.
Figure 29:
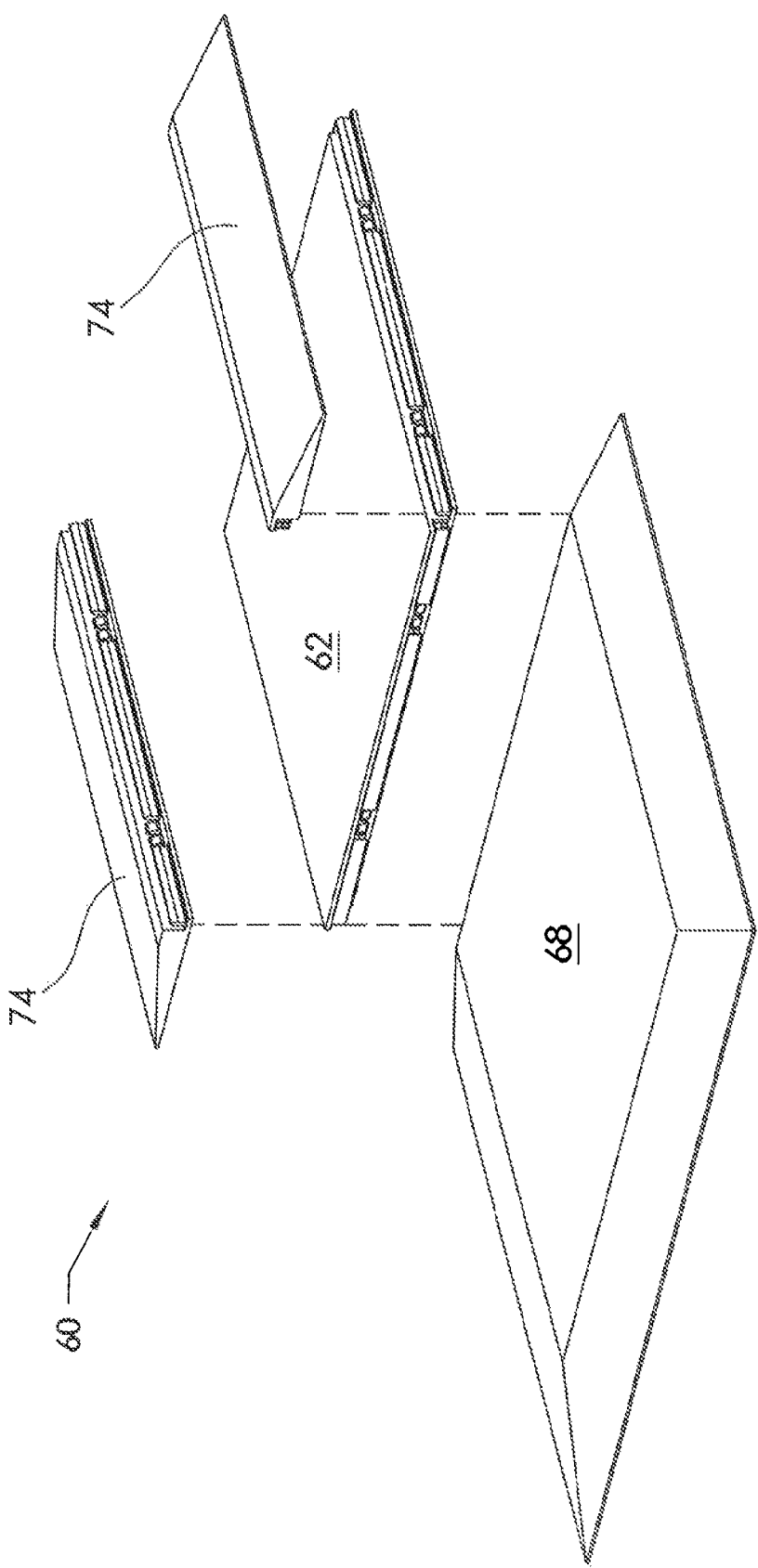
FIG. 29 is a perspective assembly exploded view of the modular instrumented panel of FIG. 1, and two edge panels, and an inert panel showing the assembly procedure.
Figure 30:
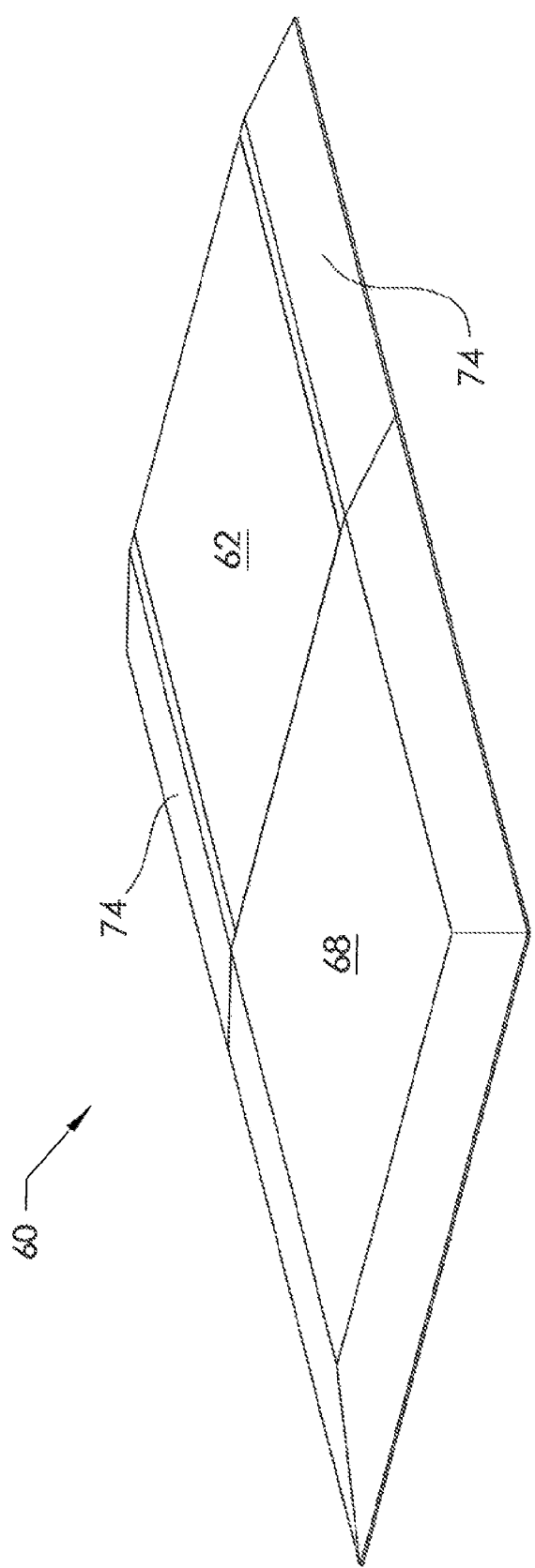
FIG. 30 is a perspective assembly contracted view of the assembly of FIG. 29.
Figure 31:
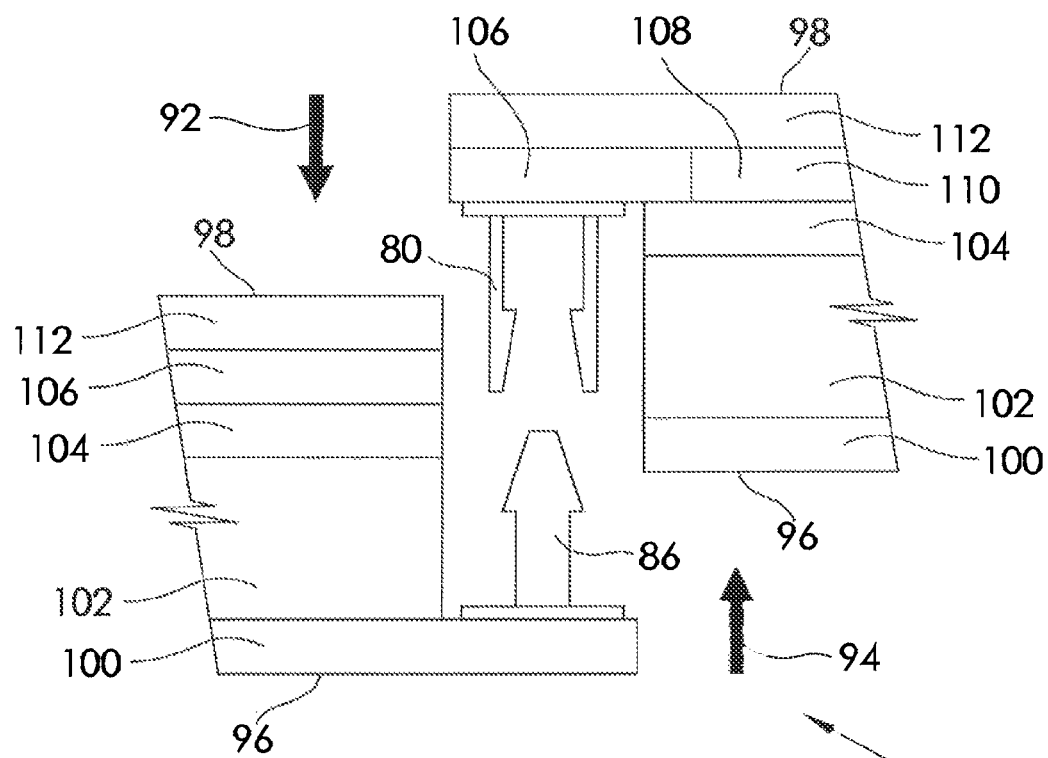
FIG. 31 is a cross-sectional elevational detail view of the modular instrumented panel assembly of FIG. 10, taken along lines 31-31 of FIG. 10, and showing the interlocking strips exploded.
Figure 32:
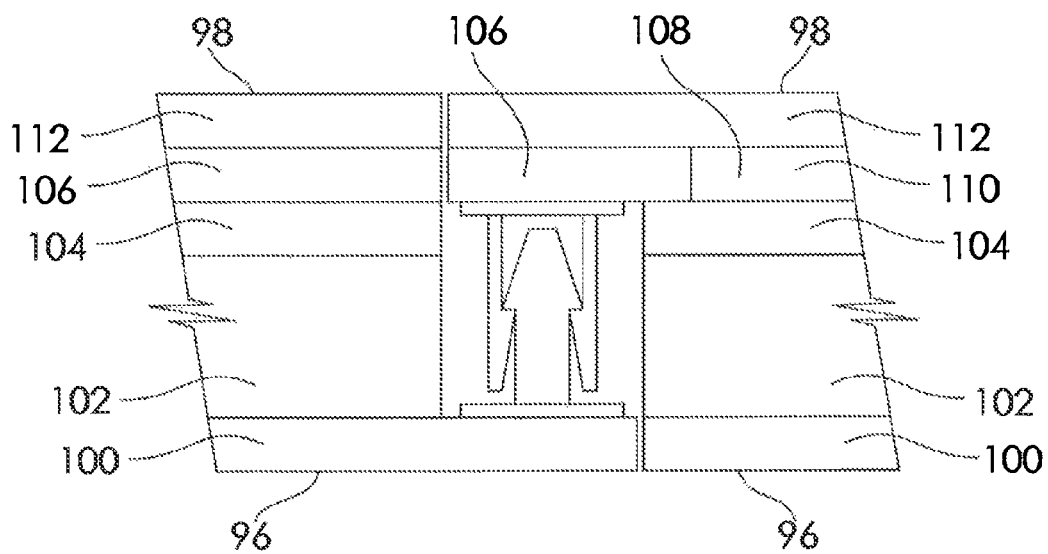
FIG. 32 is a cross-sectional elevational detail view of FIG. 31, showing the interlocking strips assembled.
Figure 33:
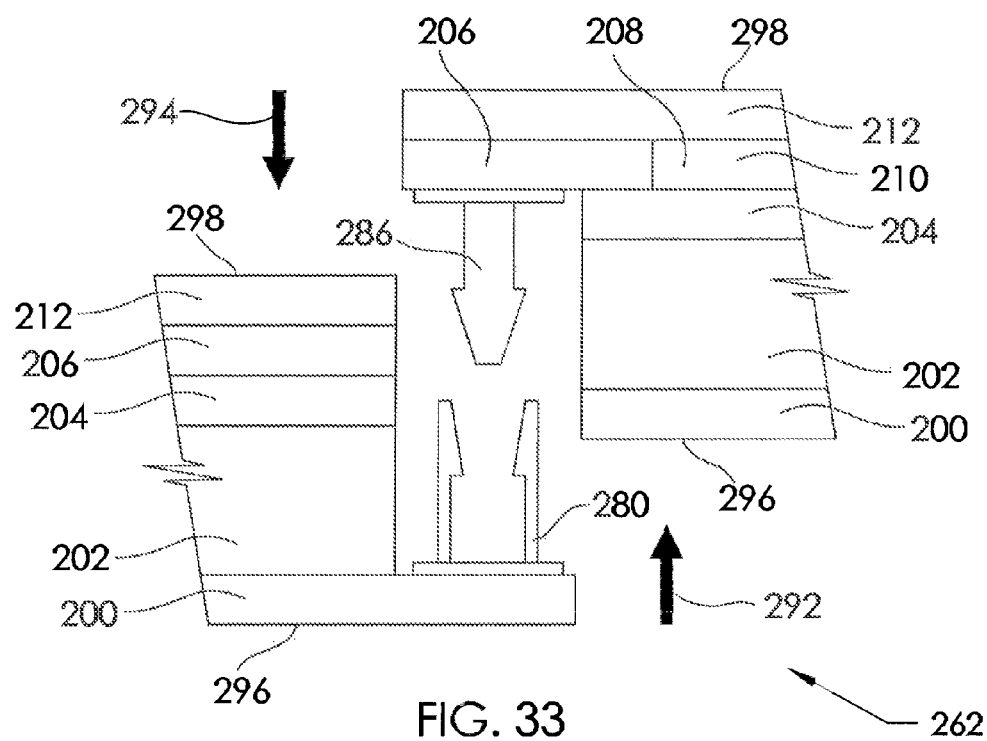
FIG. 33 is a cross-sectional elevational detail view of a modular instrumented panel assembly constructed in accordance with the invention, showing another embodiment of the interlocking strips exploded.
Figure 34:
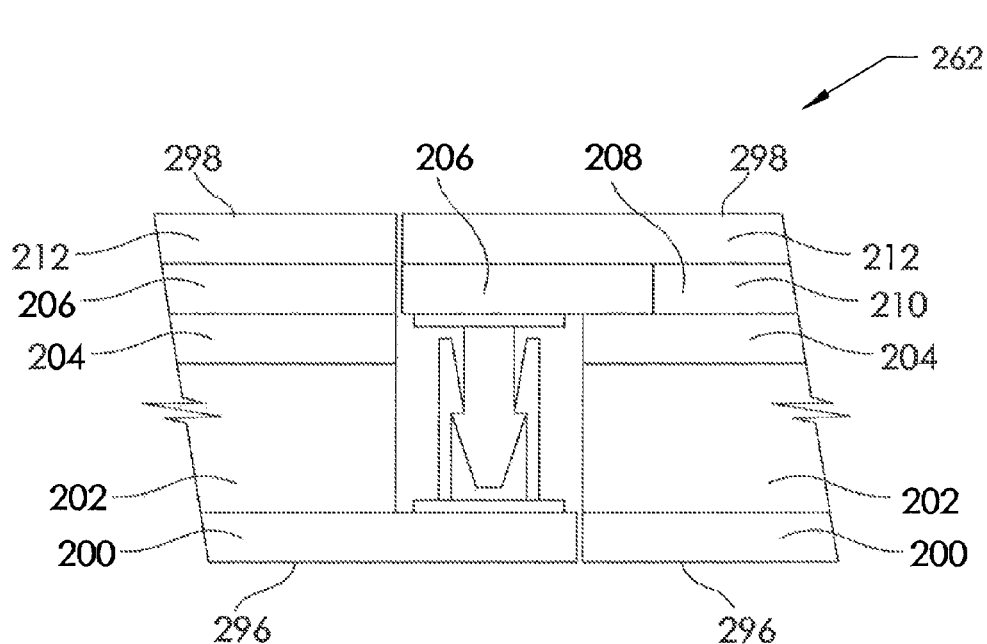
FIG. 34 is a cross-sectional elevational detail view of FIG. 33, showing the interlocking strips assembled.
Figure 35:
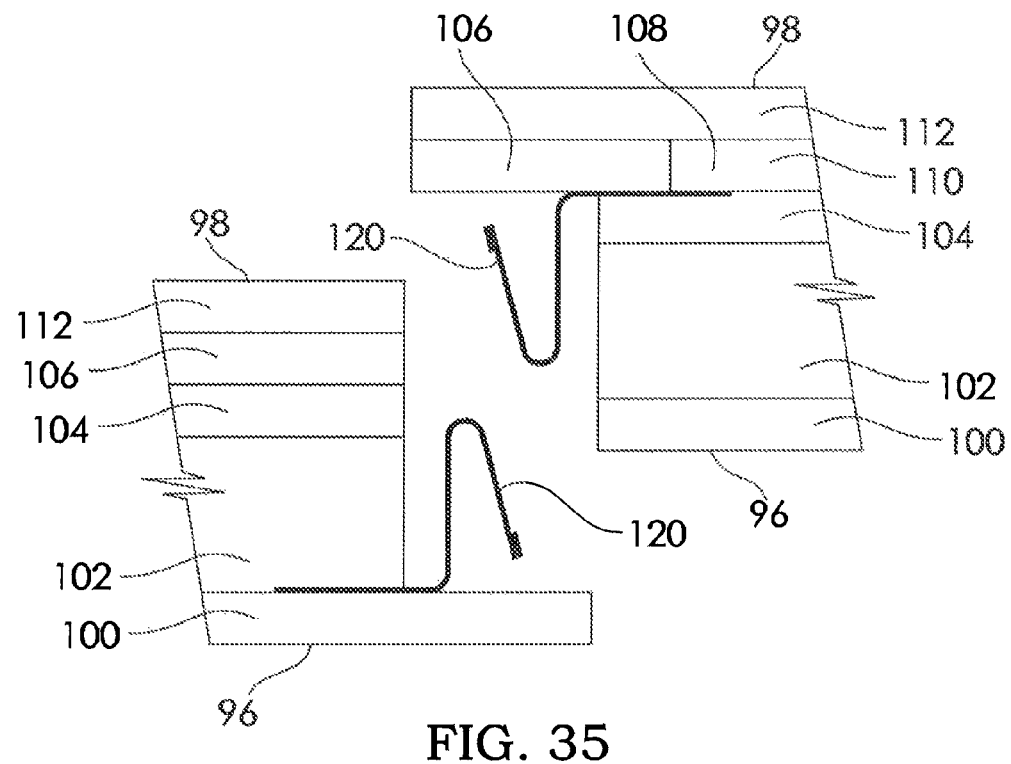
FIG. 35 is a cross-sectional elevational detail view of the modular instrumented panel of FIG. 1, taken along lines 8-8 of FIG. 1, and showing the electrical contacts exploded.
Figure 36:
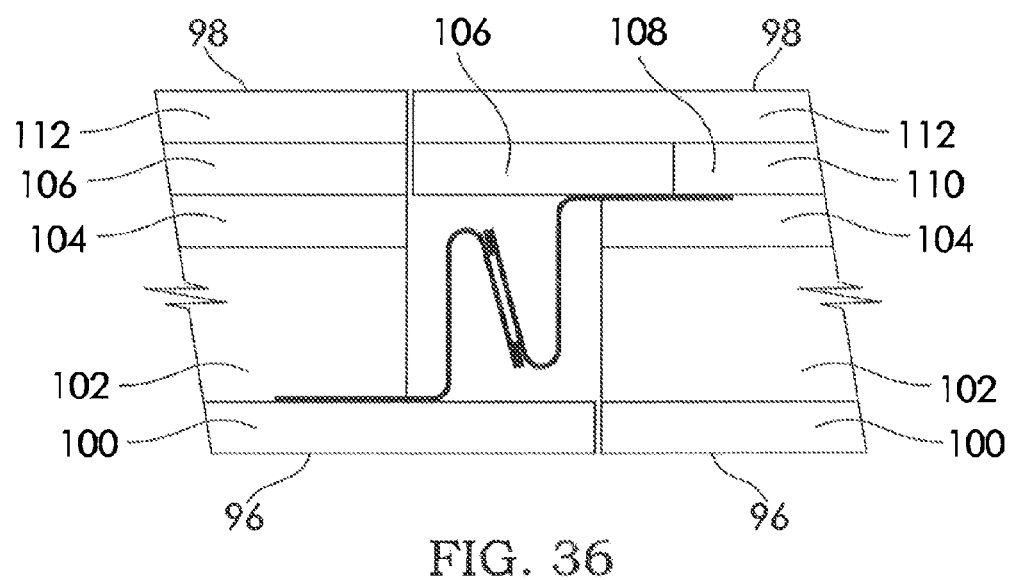
FIG. 36 is a cross-sectional elevational detail view of the modular instrumented panel of FIG. 1, taken along lines 8-8 of FIG. 1, and showing the electrical contacts engaged.
Figure 37:
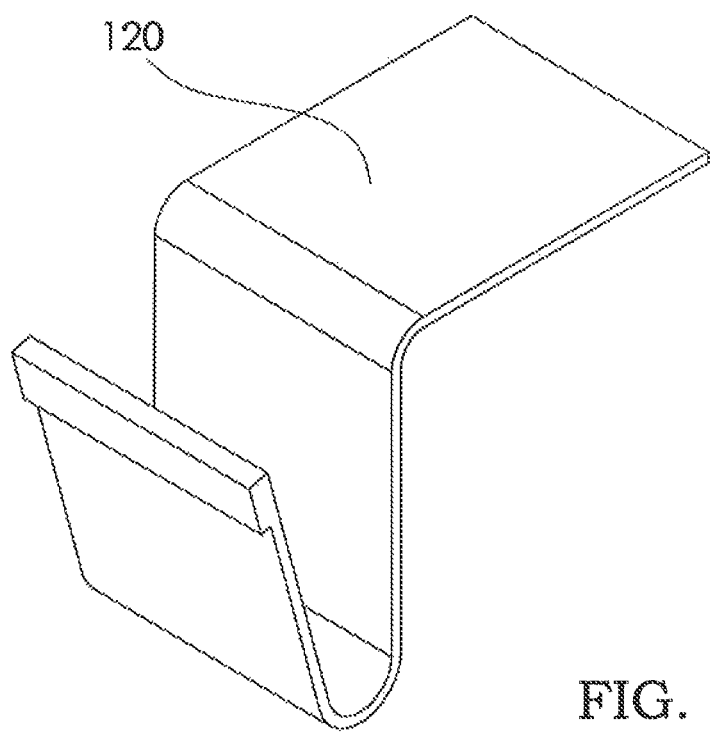
FIG. 37 is a perspective view of the electrical contact of FIG. 35.
Figure 38:
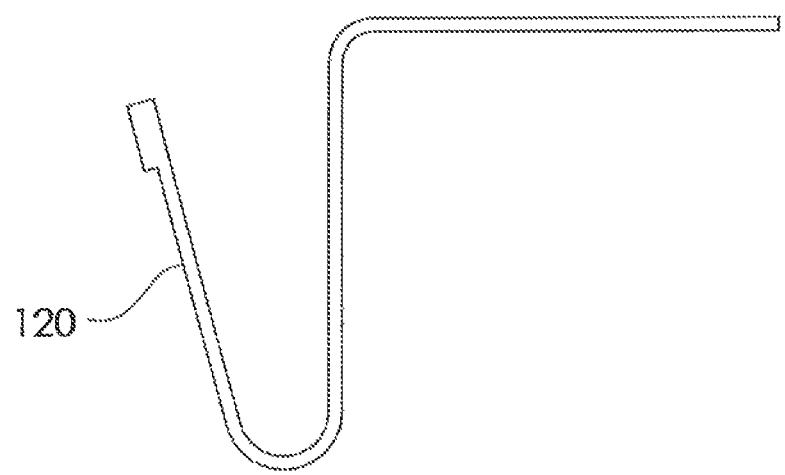
FIG. 38 is a side elevational detail view of the electrical contact of FIG. 35.
Figure 39:
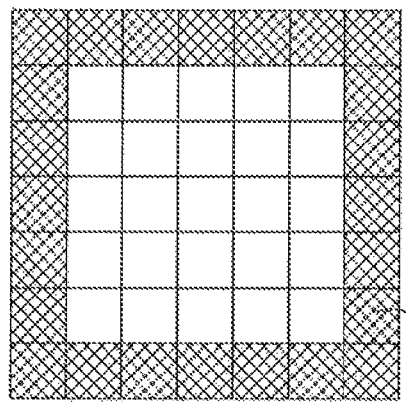
FIG. 39 is a top plan view of a perimeter pattern for use with the invention.
Figure 40:
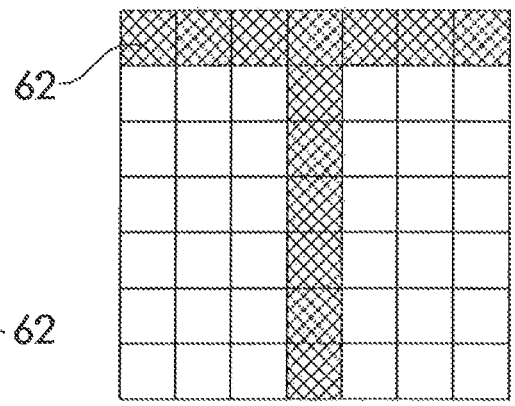
FIG. 40 is a top plan view of a T-shaped pattern for use with the invention.
Figure 41:
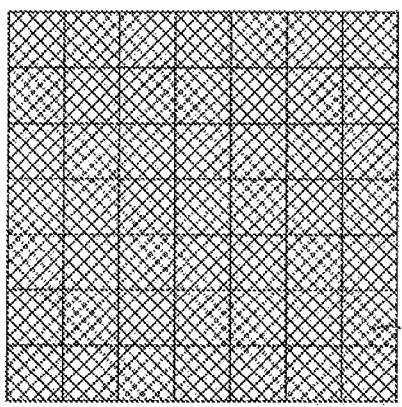
FIG. 41 is a top plan view of an area pattern for use with the invention.
Figure 42:
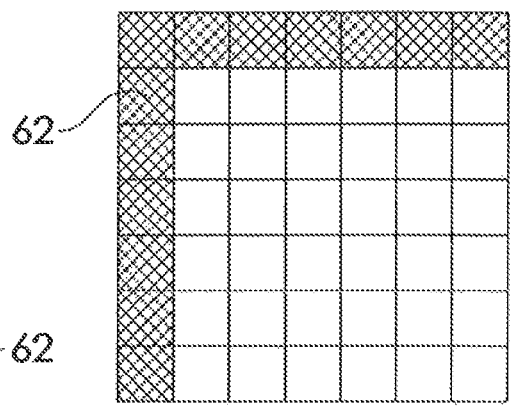
FIG. 42 is a top plan view of an L-shaped pattern for use with the invention.
Figure 43:
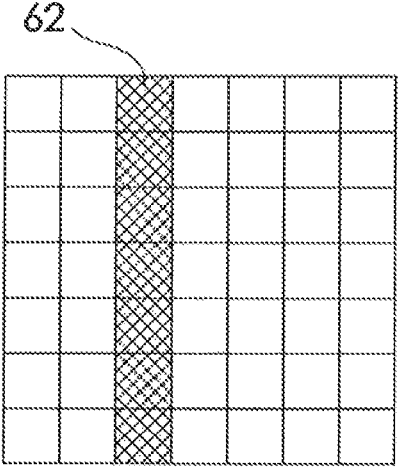
FIG. 43 is a top plan view of a straight pattern for use with the invention.
Figure 44:
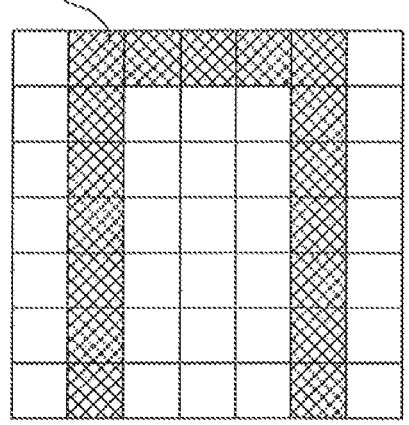
FIG. 44 is a top plan view of a U-shaped pattern for use with the invention.

Turning now to FIGS. 33 and 34, in another embodiment constructed in accordance with the invention, each sensor panel 262 is similar to sensor panel 62 described above. Sensor panel 262 includes a generally planar bottom surface 296 and an opposed top surface 298 generally parallel to the bottom surface 296. The channel strip 280 faces away from the bottom surface. This embodiment differs from sensor panel 62 described above, in that the channel strip 280 extends outward in the assembly direction 292, away from the base layer 200, and generally perpendicular to the bottom surface 296.

The arrow strip 286 faces away from the opposed top surface 298. The arrow strip 286 extends outward in the assembly direction 294 generally perpendicular to the top surface 98. The panels are assembled by pressing each panel downward in a generally vertical direction.

Each sensor panel 262 includes a generally rigid base layer 200 extending upward from the bottom surface 296. A circuit layer 202 extends upward from the base layer 200. A sensor matrix layer 204 extends upward from the circuit layer 202.

A frame layer 206 extends upward from the sensor matrix layer 204. The frame layer 206 extends perimetrically around the sensor panel 262. The frame layer 206 has an interior space 208. A fill layer 210 extends upward from the sensor matrix layer 204 coextensive with the frame layer 206. The fill layer 210 is composed of flexible material, and is disposed within the frame layer interior space 208.

A cover layer 212 extends upward from the frame layer 206 to the top surface 298. The cover layer 212 is composed of flexible material, and extends across the fill layer 210 and the frame layer 206.

The cover layer 212 and the fill layer 210 will convey the weight of the subject to the sensor matrix layer 204. The rigid or semi-rigid circuit layer 202 and base layer 200 will support the weight of the subject.

All other aspects of sensor panel 262 are similar to sensor panel 62 described above. The conductors 120, the electrical connections, the communication, and the assembly procedure are similar to that of sensor panel 62. Only the channel strip 280 and the arrow strip 286 are reversed.

Figure 45:
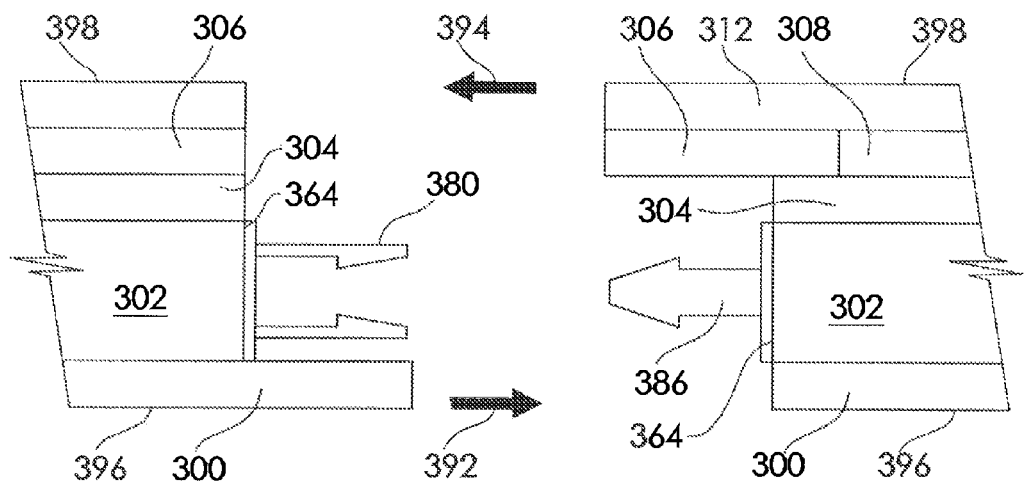
FIG. 45 is a cross-sectional elevational detail view of yet another modular instrumented panel assembly constructed in accordance with the invention, showing yet another embodiment of the interlocking strips exploded.
Figure 46:
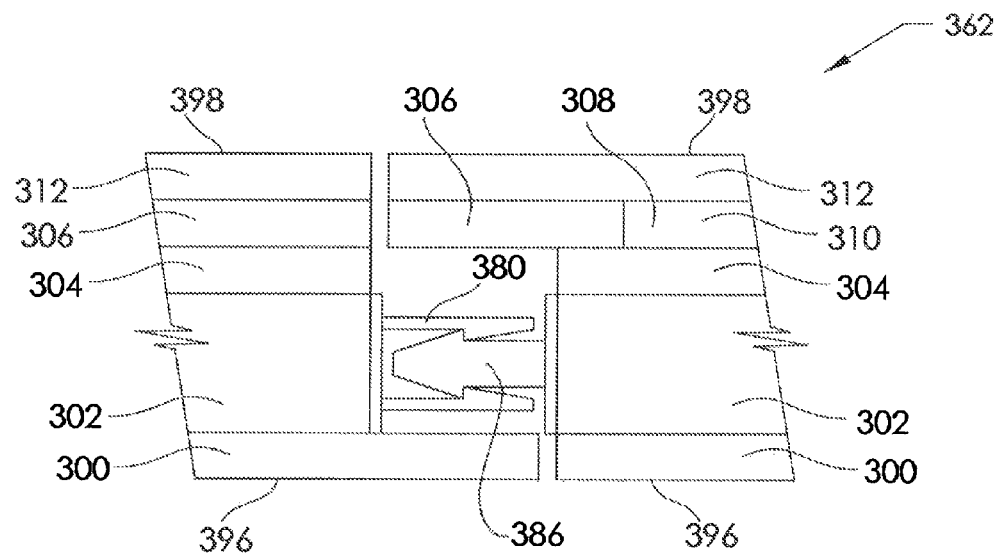
FIG. 46 is a cross-sectional elevational detail view of FIG. 45, showing the interlocking strips assembled.

Referring now to FIGS. 45 and 46, in yet another embodiment constructed in accordance with the invention, each sensor panel 362 is similar to sensor panel 62 described above. Sensor panel 362 includes a generally planar bottom surface 396 and an opposed top surface 398 generally parallel to the bottom surface 396. This embodiment differs from sensor panel 62 described above, in that the channel strip 380 extends outward from the edges 364 outward in the assembly direction 392 generally parallel to the bottom surface 396, as shown in FIGS. 45 and 46.

The arrow strip 386 extends from the edges 364 outward in the assembly direction 394 generally parallel to the bottom surface 396. Thus, the panels 362 are adapted for assembly by pressing each panel sideways in a generally horizontal direction.

Each sensor panel 362 includes a generally rigid base layer 300 extending upward from the bottom surface 396. A circuit layer 302 extends upward from the base layer 300. A sensor matrix layer 304 extends upward from the circuit layer 302.

A frame layer 306 extends upward from the sensor matrix layer 304. The frame layer 306 extends perimetrically around the sensor panel 362. The frame layer 306 has an interior space 308. A fill layer 310 extends upward from the sensor matrix layer 304 coextensive with the frame layer 306. The fill layer 310 is composed of flexible material, and is disposed within the frame layer interior space 308.

A cover layer 312 extends upward from the frame layer 306 to the top surface 398. The cover layer 312 is composed of flexible material, and extends across the fill layer 310 and the frame layer 306.

The cover layer 312 and the fill layer 310 will convey the weight of the subject to the sensor matrix layer 304. The rigid or semi-rigid circuit layer 302 and base layer 300 will support the weight of the subject.

All other aspects of sensor panel 362 are similar to sensor panel 62 described above. The conductors 120, the electrical connections, the communication, and the assembly procedure are similar to that of sensor panel 62. Only the channel strip 380 and the arrow strip 386 are rotated into a horizontal position.

Figure 47:
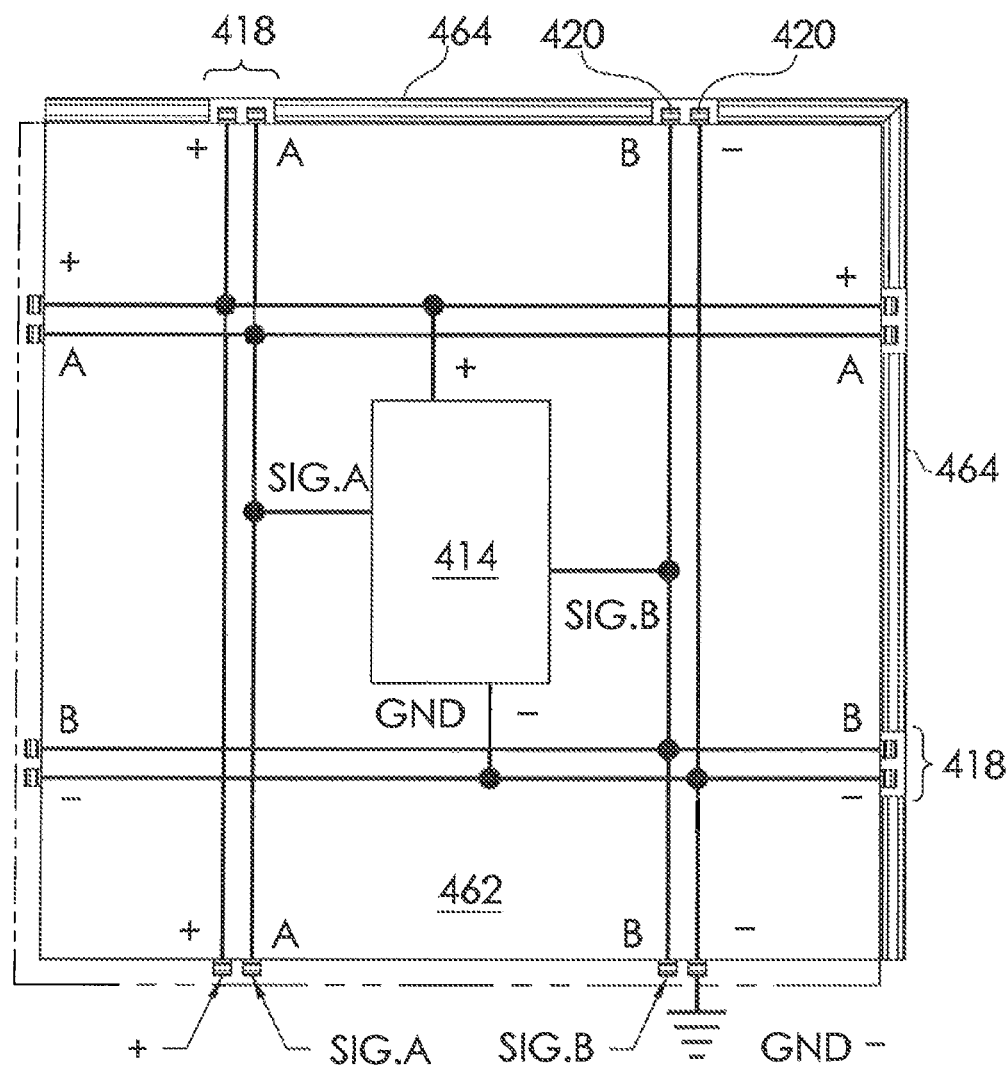
FIG. 47 is a cutaway top plan view of still another modular instrumented panel constructed in accordance with the invention, and showing the signal over power connections in the panel.
Figure 48:
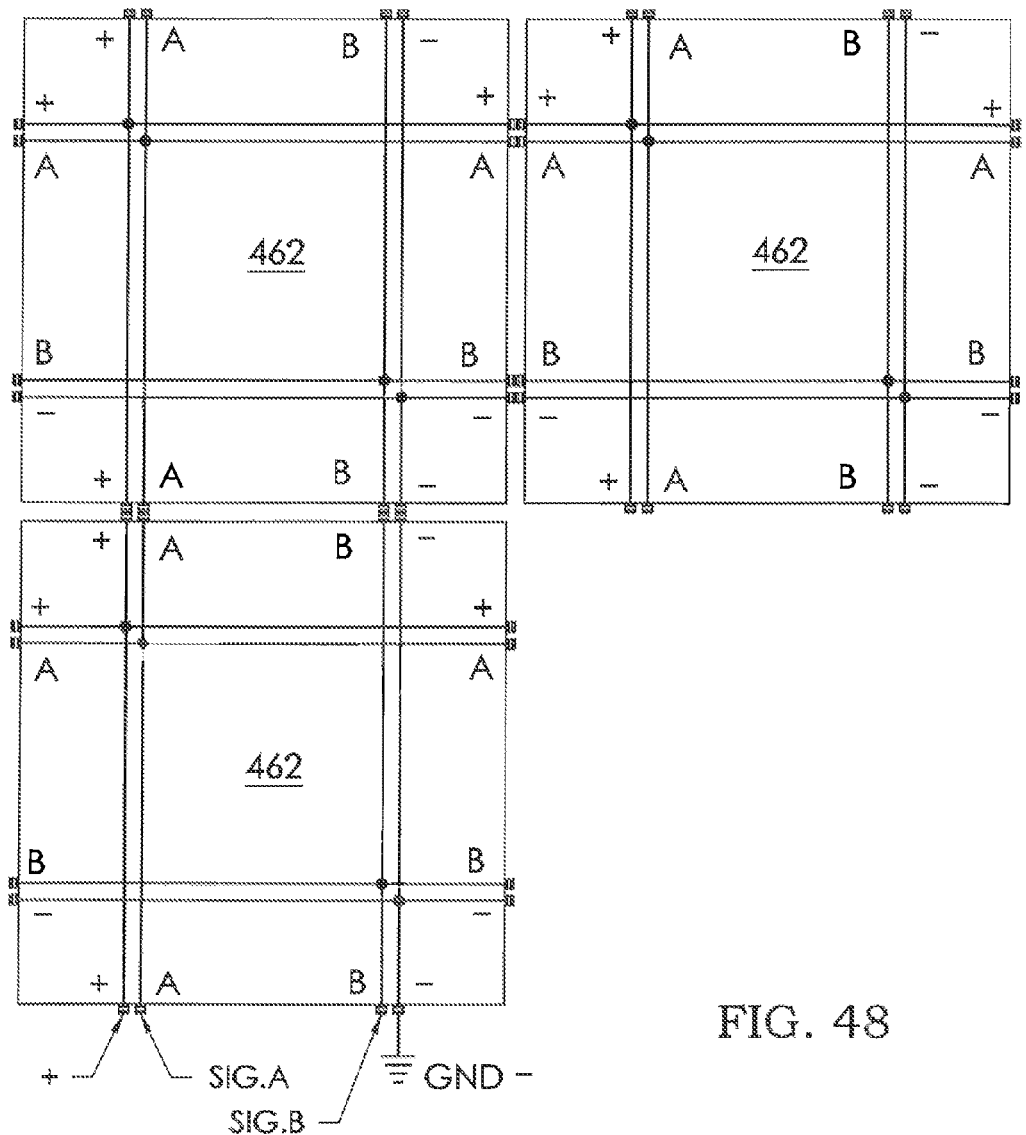
FIG. 48 is a cutaway top plan view of the modular instrumented panel of FIG. 47, and showing the power and signal connections between assembled panels.
Figures 49, 50:
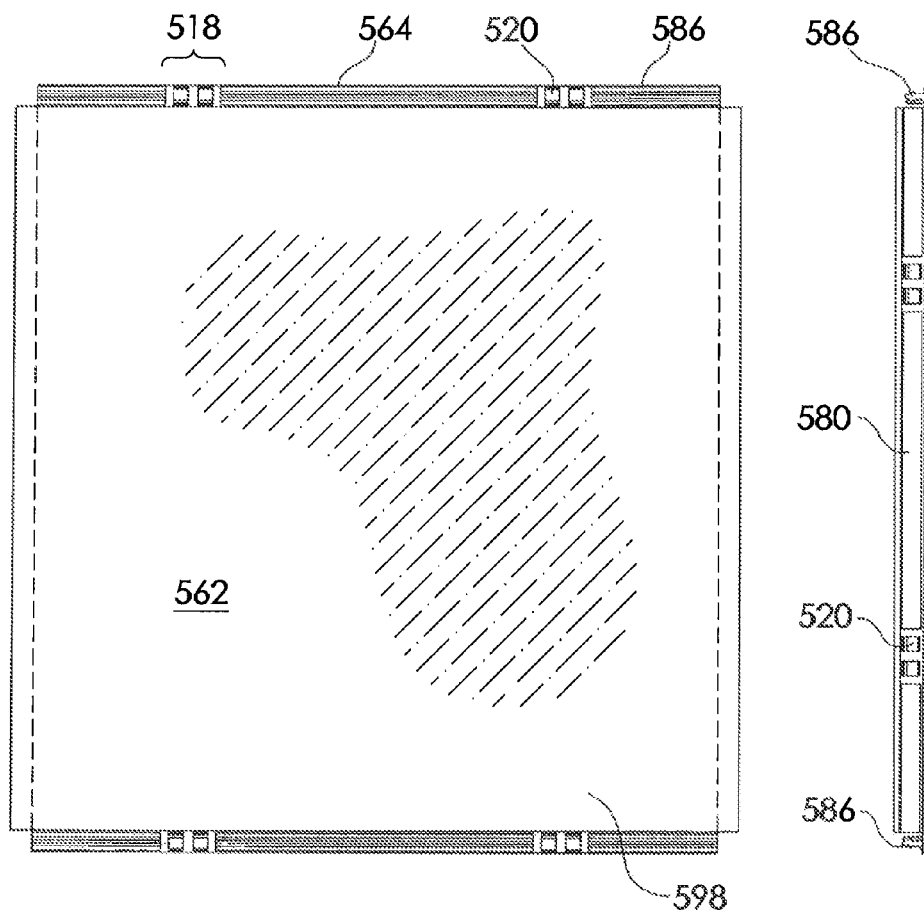
FIG. 49 is a top plan view of a further modular instrumented floor covering panel constructed in accordance with the invention.
FIG. 50 is a right side view of the modular instrumented panel of FIG. 49.
Figure 51:
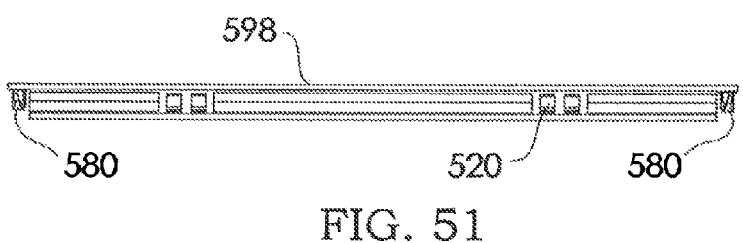
FIG. 51 is a front elevational view of the modular instrumented panel of FIG. 49.

Referring now to FIGS. 47 and 48, in still another embodiment constructed in accordance with the invention, each sensor panel 462 is similar to sensor panel 62 described above. Sensor panel 462 differs from sensor panel 62 in that sensor panel 462 utilizes a "Signal Over Power" method for the transmission of the data or signal. Each pair of electrical connectors 418 has two conductors 420 as before, but they are connected differently. One outside conductor 420 is for positive voltage. The opposite outside conductor 420 is for ground and negative voltage. The two inside conductors 420 are for data. In FIG. 47, signal A and signal B are for data, with the ground being common for both data and power.

FIG. 48 shows how the individual sensor panels 462 are connected together to convey power and signal from each panel to adjacent panels. One example of the protocol that can be used is RS-485, well known to those skilled in the art. All other aspects of sensor panel 462 are similar to sensor panel 62 described above. The conductors 420, arrow strips 86, channel strips 80, and the assembly procedure are similar to that of sensor panel 62. It is to be understood that alternative elements, such as arrow strips 286 and 386, and channel strips 280 and 380, as well as other alternative elements described above, can be utilized with sensor panels 462 and all other sensor panels disclosed, and are to be considered equivalent embodiments within the spirit and scope of the claims.

Referring now to FIGS. 49-54, in still another embodiment constructed in accordance with the invention, each sensor panel 562 is similar to sensor panel 62 described above. Sensor panel 562 differs from sensor panel 62 in that the elongated channel strip 580 extends along two opposed edges 564 of each sensor panel 562. The elongated arrow strip 586 extends along the remaining two opposed edges 564 of each sensor panel 562.

All other aspects of sensor panel 562 are similar to sensor panel 62 described above. The electrical connectors 518, conductors 520, arrow strips 586, and channel strips 580, are similar to that of sensor panel 62. The assembly procedure differs in that adjacent panels must be rotated 90° in either direction, so that the opposed arrow strips 586, and channel strips 580, will engage. Other alternative elements described above can be utilized with sensor panels 562, and are to be considered equivalent embodiments within the spirit and scope of the claims.

Referring now to FIGS. 55-80, as well as FIGS. 39-44, yet another modular instrumented floor covering assembly 660 constructed in accordance with the invention is used in connection with a subject (not shown) walking across the assembly. The floor covering assembly 660 is similar to floor covering assembly 60 described above in that floor covering assembly 660 comprises a plurality of sensor panels 662 having interlocking edges 664. The sensor panels 662 are adapted for interlocking the adjacent panels together along the edges 664. Each sensor panel 662 has a pressure sensor matrix 666 responsive to a weight of the subject for generating data relating to movement of the subject. The plurality of sensor panels 662 is adapted for selective and releasable assembly in patterns, as shown in FIGS. 39-44.

Sensor panel 662 includes a generally planar bottom surface 696 and an opposed top surface 698 generally parallel to the bottom surface, each edge 664 of the sensor panel 662 being generally perpendicular to the bottom surface 696. A generally rigid base layer 600 extends upward from the bottom surface 696. A circuit layer 602 is disposed above the base layer 600 and extends upward therefrom. A sensor matrix layer 604 is disposed above the circuit layer 602 and extends upward from the circuit layer 602. A cover layer 612 is disposed above the sensor matrix layer 604. The cover layer 612 is made from a material adapted for walking upon, for example: carpet; rubber; canvas; or linoleum. The material must be flexible, so that the cover layer 612 will convey the weight of the subject to the sensor matrix layer 604. The base layer 600 is generally rigid, strong, and firm enough to support the weight of the subject and bridge small gaps or irregularities in the floor.

The structure for interlocking adjacent panels together includes magnets, each magnet having a central axis, and opposed north and south poles aligned with the central axis. A first magnet 680 is disposed on each interlocking edge 664 of each sensor panel 662. The first magnet 680 has a north pole 682 facing transversely outward from and aligned with the panel edge 664. The first magnet 680 has a south pole 684 facing opposite to the north pole 682. A second magnet 686 is disposed on each interlocking edge 664 of each sensor panel 662. The second magnet 686 has a south pole 690 facing transversely outward from and aligned with the panel edge 664. The second magnet 686 has a north pole 688 facing opposite to the south pole 690. The first 680 and second 686 magnets are identical, but facing opposite directions. Each of the first 680 and second 686 magnets is circular about the central axis, and preferably toroidal in shape. A bore 692, 694 extends through each of the first 680 and second 686 magnets respectively, and is aligned with the central axis of each magnet.

The first magnet north pole 682 of each sensor panel 662 is adapted for alignment with the second magnet south pole 690 of an interlocking adjacent panel 662. Similarly, the second magnet south pole 690 of each sensor panel 662 is adapted for alignment with the first magnet north pole 682 of the interlocking adjacent panel 662. Since opposite magnetic poles attract one another, this alignment of magnets will attract the sensor panels toward one another. Simultaneously, the polar axis alignment of the adjacent magnets will become collinear. This will also generally align the sensor panels with one another in two orthogonal axes perpendicular to the polar axes, both vertically and horizontally. The adjacent sensor panels will be drawn together and releasably attached to one another. As the magnets contact, the panels will then be aligned in the third axis. Thus, the sensor panels are self-aligning in three orthogonal directions by the novel arrangement of magnets. The panels can be assembled by bringing them together vertically, horizontally, or diagonally. As the panels approach one another, they will align and move together. The sensor panels can be released just as easily to replace a damaged panel, or to lay down a different pattern.

The power means 618 includes at least one pair of electrical connectors 618 disposed on each edge 664 of each of the sensor panels 662. Optionally, two pairs of electrical connectors 618 will be employed to ensure the connection. A one of the pair is for positive voltage, and the remaining one of the pair is for negative voltage. Typically, two groups of three of the electrical connectors 618 will be employed to ensure the connection, for six total electrical connectors 618 on each interlocking edge 664. Two of the group are for positive voltage, and the remaining one is for negative voltage and ground. The electrical connections in two groups of three on each edge 664 are shown in FIG. 64. This arrangement ensures that the panels can be placed in any orientation, even rotated 90° or 180°, and still reliably connect with the proper polarity. The redundant connectors 618 ensure that the system remains in service in the event of dirt or corrosion on some of the connectors 618. The connectors 618 on adjacent sensor panels are adapted for operatively electrically and releasably connecting together upon interlocking any two adjacent panels together along the edges. The connectors 618 each have a conductor 620 on the sensor panel interlocking edge 664. Each conductor 620 is adapted for contacting a similar conductor 620 on the adjacent sensor panel interlocking edge 664 with spring bias. The electrical connections in two pairs on each edge 664 are shown in FIG. 80.

The conductor 620 is a cylindrical pin 630 extending between a generally spheroidal first end 632 and a second end 634. A collar 636 is attached to the pin 630 and spaced apart from the first end 632. A coil spring 638 surrounds the pin 630 and is disposed against the collar 636 to push or bias the pin 630 in the direction of the first end 632. The connector 618 is aligned with the magnet central axis. The pin 630 is received in each magnet bore 692, 694 with the pin first end 632 projecting outward beyond the magnet. The first 680 and second 686 magnets are disposed within the base layer 600 with the central axis generally perpendicular to the sensor panel edge 664. The north 682 and south poles 690 of the first 680 and second 686 magnets respectively are aligned generally flush with the sensor panel edge 664. The pin first end 632 projects outward beyond the sensor panel edge 664.

Upon assembly, the edge 664 of a sensor panel 662 will be juxtaposed with the edge 664 of an adjacent sensor panel 662. The central axis of the first 680 and second 686 magnets will generally align collinear with the central axis of magnets of opposite polarity on the adjacent panel. The magnets on adjacent panels will attract and draw the panels together so as to generally self-align in three directions along vertical, horizontal, and the central axes. The magnets will releasably hold the panels together. The connectors 618 on adjacent panels will align with one another. The first ends 632 of the opposed cylindrical pins 630 on adjacent panels will come into contact with one another under spring bias. This will provide operative electrical connection between adjacent panels.

At least one inert panel 668 is provided, as shown in FIGS. 68-78. The inert panel 668 is a "dummy" panel, in that it has no instrumentation, no sensor array, and no circuit board. It typically has no wireless transmitter, but the transmitter is an option. The inert panel 668 may have wiring and electrical connectors to provide electrical continuity to adjacent panels. The inert panel 668 allows the subject to take one or two steps toward the instrumented array, in order to achieve alignment and a steady pace. The inert panel 668 has one interlocking edge 670. The inert panel 668 is adapted for interlocking with one of the sensor panels 662 along the interlocking edge 664. The inert panel 668 has a beveled edge 672 along the three remaining edges so as to preclude tripping the subject.

In another embodiment of the inert panel 669 shown in FIGS. 72 and 73, the inert panel 669 has one beveled edge 672 and three interlocking edges 670. Optional inert panel 669 connects to optional edge panel 675 described below. The combination will provide power near power outlets located in the corners of a room.

A first magnet 680 is disposed on each interlocking edge 670 of each inert panel 668. The first magnet 680 has a north pole 682 facing transversely outward from and aligned with the panel edge 670. The first magnet 680 has a south pole 684 facing opposite to the north pole 682. A second magnet 686 is disposed on each interlocking edge 670 of each inert panel 668. The second magnet 686 has a south pole 690 facing transversely outward from and aligned with the panel edge 670. The second magnet 686 has a north pole 688 facing opposite to the south pole 690. The first 680 and second 686 magnets are identical, but facing opposite directions. Each of the first 680 and second 686 magnets is circular about the central axis, and preferably toroidal in shape. A bore 692, 694 extends through each of the first 680 and second 686 magnets respectively, and is aligned with the central axis of each magnet. The second magnet south pole 690 of the inert panel 668, 669 is adapted for alignment with the first magnet north pole 682 of the interlocking adjacent sensor panel 662. In a similar manner to that described above, the inert panel 668, 669 and the sensor panel 662 will be attracted toward one another. The inert panel 668, 669 and the sensor panel 662 will be generally aligned with one another. The inert panel 668, 669 and the sensor panel 662 will be releasably attached to one another.

The inert panel 668 includes at least one pair of electrical connectors 618 disposed on the interlocking edge 670 of the inert panel 668. Optionally, two pairs of electrical connectors 618 will be employed to ensure the connection. A one of the pair is for positive voltage, and the remaining one of the pair is for negative voltage. Typically, two groups of three of the electrical connectors 618 will be employed to ensure the connection, for six total electrical connectors 618 on each interlocking edge 670. Two of the group are for positive voltage, and the remaining one is for negative voltage and ground. The electrical connections are shown in FIG. 64. This arrangement ensures that the panels can be arranged in any orientation, and still reliably connect. The connectors 618 on the inert panel 668 are adapted for operatively electrically and releasably connecting to adjacent panels upon interlocking any two adjacent panels together along the edges. The connectors 618 each have a conductor 620 on the interlocking edge 670. Each conductor 620 is adapted for contacting a similar conductor 620 on the adjacent sensor panel interlocking edge 664 with spring bias. The connectors 618 and conductors 620 are as described above.

Another embodiment of the inert panel (not shown) would have all four edges being interlocking edges 670. None of the edges would be beveled. This panel would fill in the field of a full floor pattern wherein the instrumented sensor panels 662 follow a narrow path across the floor. The inert panels would provide continuity and a uniform surface from the sensor panel's path across to the walls.

At least one edge panel 674 is provided having one interlocking edge 676. Typically, the edge panel 674 is adapted for interlocking with one of the sensor panels 662 along the interlocking edge 664. The edge panel 674 is a "dummy" panel, in that it has no instrumentation, no sensor array, and no circuit board. It typically has no wireless transmitter, but the transmitter is an option. The edge panel 674 has wiring and electrical connectors to provide electrical continuity to adjacent sensor panels 662. The edge panel 674 has a beveled edge 678 opposing the interlocking edge 676 so as to preclude tripping the subject.

In another embodiment of the edge panel 675 shown in FIGS. 74-77, the edge panel 675 has two adjacent beveled edges 672 that meet in a "hip roof" configuration. Edge panel 675 has one interlocking edge 670. The purpose of edge panel 675 is to provide power to the optional inert panel 669. Such power outlets are often located in the corners of a room.

A first magnet 680 is disposed on each interlocking edge 676 of each edge panel 674. The first magnet 680 has a north pole 682 facing transversely outward from and aligned with the panel edge 676. The first magnet 680 has a south pole 684 facing opposite to the north pole 682. A second magnet 686 is disposed on each interlocking edge 676 of each edge panel 674. The second magnet 686 has a south pole 690 facing transversely outward from and aligned with the panel edge 676. The second magnet 686 has a north pole 688 facing opposite to the south pole 690. The first 680 and second 686 magnets are identical, but facing opposite directions. Each of the first 680 and second 686 magnets is circular about the central axis, and preferably toroidal in shape. A bore 692, 694 extends through each of the first 680 and second 686 magnets respectively, and is aligned with the central axis of each magnet. The second magnet south pole 690 of the edge panel 674 is adapted for alignment with the first magnet north pole 682 of the interlocking adjacent sensor panel 662. In a similar manner to that described above, the edge panel 674 and the sensor panel 662 will be attracted toward one another. The edge panel 674 and the sensor panel 662 will be generally aligned with one another. The edge panel 674 and the sensor panel 662 will be releasably attached to one another.

The power means includes at least one pair of electrical connectors 618 disposed on the interlocking edge 676 of the edge panel 674. Optionally, two pairs of electrical connectors 618 will be employed to ensure the connection. A one of the pair is for positive voltage, and the remaining one of the pair is for negative voltage. Typically, two groups of three of the electrical connectors 618 will be employed to ensure the connection, for six total electrical connectors 618 on each interlocking edge 676. Two of the group are for positive voltage, and the remaining one is for negative voltage and ground. The electrical connections are shown in FIG. 64. This arrangement ensures that the panels can be arranged in any orientation, and still reliably connect. The connectors 618 on the edge panel 674 are adapted for operatively electrically and releasably connecting to connectors 618 on the adjacent sensor panels upon interlocking any two adjacent panels together along the edges. The connectors 618 each have a conductor 620 on the edge panel interlocking edge 676. Each conductor 620 is adapted for contacting a similar conductor 620 on the adjacent sensor panel interlocking edge 664 with spring bias. The connectors 618 and conductors 620 are as described above. A power supply 622 is provided, along with wiring 624 and a plug 626. The power supply 622 will operatively electrically and releasably connect the power source (not shown) to the electrical connectors 618 on the edge panel 674. The power supply 622 will typically convert line power AC to low voltage DC to supply the instrumentation. For example, line power can be 120 or 240 volts AC, and the circuit boards can use 5 volts DC.

Communicating means 614, 616, is provided for communicating data between adjacent sensor panels and from the sensor panels to an outside computer (not shown). Data from the sensor array can be sent between panels and outward from the panel assembly by hardwired means or by wireless means. A transmitter 616 is immersed in the circuit layer 602 and operatively electrically connected to the circuit board 614 for transmitting data wirelessly. The wireless transmitter 616 is typically a wireless local area network (WLAN or Wi-Fi®) transceiver, and is well known by those skilled in the art. The data is sent to an outside computer (not shown) for analysis.

It will be appreciated that variants of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

PARTS LIST

Modular Instrumented Floor Covering

Part No. Description
60 floor covering assembly
62 sensor panels
64 sensor panel interlocking edges
66 pressure sensor matrix
68 inert panel
70 inert panel interlocking edge
72 inert panel beveled edge
74 edge panel
76 edge panel interlocking edge
78 edge panel beveled edge
80 channel strip
82 channel strip tapered opening
84 channel strip inside shoulder
86 arrow strip
88 arrow strip tapered outer portion
90 arrow strip outside shoulder
92 channel strip assembly direction
94 arrow strip assembly direction
96 sensor panel bottom surface
98 sensor panel top surface
99 handholes
100 base layer
102 circuit layer
104 sensor matrix layer
106 frame layer
108 frame layer interior space
110 fill layer
112 cover layer
114 circuit board
116 transmitter
118 electrical connectors
120 conductor strips
122 power supply
124 wires
126 plug
200 base layer
202 circuit layer
204 sensor matrix layer
206 frame layer
208 frame layer interior space
210 fill layer
212 cover layer
262 sensor panels
280 channel strip
286 arrow strip
292 channel strip assembly direction
294 arrow strip assembly direction
296 sensor panel bottom surface
298 sensor panel top surface
300 base layer
302 circuit layer
304 sensor matrix layer
306 frame layer
308 frame layer interior space
310 fill layer
312 cover layer
362 sensor panels
380 channel strip
386 arrow strip
392 channel strip assembly direction
394 arrow strip assembly direction
396 sensor panel bottom surface
398 sensor panel top surface
414 circuit board
418 electrical connectors
420 conductor strips
462 sensor panels
464 sensor panel interlocking edges
518 electrical connectors 520 conductor strips
562 sensor panels
564 sensor panel interlocking edges
580 channel strip
586 arrow strip
596 sensor panel bottom surface
598 sensor panel top surface
599 handholes
600 base layer
602 circuit layer
604 sensor matrix layer
612 cover layer
614 circuit board
616 transmitter
618 electrical connectors
620 conductor
622 power supply
624 wires
626 plug
630 pin
632 pin first end
634 pin second end
636 collar
638 spring
660 floor covering assembly
662 sensor panels
664 sensor panel interlocking edges
666 pressure sensor matrix
668 inert panel
669 alternate inert panel
670 inert panel interlocking edge
672 inert panel beveled edge
674 edge panel
675 alternate edge panel
676 edge panel interlocking edge
678 edge panel beveled edge
680 first magnet
682 first magnet north pole
684 first magnet south pole
686 second magnet
688 second magnet north pole
690 second magnet south pole
692 first magnet bore
694 second magnet bore
696 sensor panel bottom surface
698 sensor panel top surface

What is claimed is:

1. A modular instrumented floor covering assembly for use in connection with a subject walking across the assembly for generating data relating to movement of the subject, a power source, and a computer, the floor covering assembly comprising:
a plurality of sensor panels having interlocking edges, the sensor panels being adapted for interlocking adjacent panels together along the edges, each sensor panel having a pressure sensor matrix responsive to a weight of the subject, the plurality of sensor panels being adapted for selective and releasable assembly in patterns;
a first magnet and a second magnet spaced apart on each interlocking edge of each sensor panel, so as to attract the sensor panels toward one another and generally align the sensor panels with one another and releasably attach the sensor panels to one another;
communicating means for communicating data from the sensor panels and between adjacent sensor panels, the communicating means being selected from the group consisting of hardwired means and wireless means; and
power means for supplying power to the sensor panels and between adjacent sensor panels, the power means comprising a power supply.

2. The modular instrumented floor covering assembly of claim 1, further comprising:
at least one inert panel having one interlocking edge, the inert panel being adapted for interlocking with one of the sensor panels along the interlocking edge, the inert panel edge opposite the sensor panel being an outermost edge of the assembly and being a beveled edge so as to preclude tripping the subject; and
a first magnet and a second magnet spaced apart on each interlocking edge of each inert panel, so as to attract the inert panels toward the sensor panels and generally align the panels with one another and releasably attach the inert panels to the sensor panels; and wherein
the inert panel has no pressure sensor matrix.

3. The modular instrumented floor covering assembly of claim 1, wherein the power means further comprises at least one pair of electrical connectors disposed on each edge of each of the sensor panels, a one of the pair being for positive voltage, and a remaining one of the pair being for negative voltage, the connectors on adjacent sensor panels being adapted for operatively electrically and releasably connecting together upon interlocking adjacent panels together along the edges, the connectors having a conductor on the sensor panel interlocking edge adapted for contacting a conductor on the adjacent sensor panel interlocking edge with spring bias.

4. The modular instrumented floor covering assembly of claim 3, further comprising:
at least one edge panel having one interlocking edge, the edge panel being adapted for interlocking with one of the sensor panels along the interlocking edge, the edge panel edge opposite the sensor panel being an outermost edge of the assembly and being a beveled edge so as to preclude tripping the subject; and
a first magnet and a second magnet spaced apart on each interlocking edge of each edge panel, so as to attract the edge panels toward the sensor panels and generally align the panels with one another and releasably attach the edge panels to the sensor panels; and wherein
the edge panel has no pressure sensor matrix.

5. The modular instrumented floor covering assembly of claim 4, wherein the power means further comprises:
at least one pair of electrical connectors disposed on the interlocking edge of the edge panel, a one of the pair being for positive voltage, and a remaining one of the pair being for negative voltage, the electrical connectors being adapted for operatively electrically and releasably connecting the electrical connectors on the edge panel to the electrical connectors on one adjacent sensor panel, the connectors having a conductor on the edge panel interlocking edge adapted for contacting a conductor on the adjacent sensor panel interlocking edge with spring bias; and
the power supply being adapted for operatively electrically and releasably connecting the power source to the electrical connectors on the edge panel.

6. The modular instrumented floor covering assembly of claim 3, further comprising:
the first magnet having a north pole facing transversely outward from the panel edge, the first magnet being juxtaposed with the panel edge; and the second magnet having a south pole facing transversely outward from the panel edge, the second magnet being juxtaposed with the panel edge; wherein the first magnet north pole of each sensor panel being adapted for alignment with the second magnet south pole of an interlocking adjacent panel; and the second magnet south pole of each sensor panel being adapted for alignment with the first magnet north pole of the interlocking adjacent panel; so as to attract the sensor panels toward one another and juxtapose the sensor panels with one another and releasably attach the sensor panels to one another.

7. The modular instrumented floor covering assembly of claim 6, wherein the connectors each further comprise:
a cylindrical pin extending between a first end and a second end, the cylindrical pin being the conductor;
a collar attached to the pin and spaced apart from the first end; and
a spring disposed against the collar.

8. The modular instrumented floor covering assembly of claim 7, further comprising:
each of the first and second magnets being toroidal in shape, each magnet having a central axis, and opposed north and south poles aligned with the central axis, and a bore through the magnet aligned with the central axis;
the cylindrical pin first end being spheroidal; and
the connector being aligned with the magnet central axis, with the pin received in the bore and the pin first end projecting outward beyond the magnet; wherein
the pin is biased by the spring in the direction of the first end.

9. The modular instrumented floor covering assembly of claim 8, wherein each sensor panel further comprises:
a flat bottom surface and an opposed flat top surface, each edge of the sensor panel being transverse to the bottom surface;
a base layer sufficiently rigid to support the weight of the subject, the base layer extending upward from the bottom surface;
a circuit layer disposed above the base layer and extending upward;
a sensor matrix layer disposed above the circuit layer and extending upward;
a cover layer disposed above the sensor matrix layer, the cover layer being material adapted for walking upon; so that the cover layer will convey the weight of the subject to the sensor matrix layer, and the base layer will support the weight of the subject;
the first and second magnets being disposed within the base layer with the central axis transverse to the sensor panel edge, and the north and south poles respectively being juxtaposed with the sensor panel edge;
the pin first end projecting outward beyond the sensor panel edge; so that
upon assembly the edge of a sensor panel will be juxtaposed with the edge of an adjacent sensor panel, the central axis of the first and second magnets will be juxtaposed with the central axis of magnets of opposite polarity on the adjacent panel, the magnets on adjacent panels will attract and draw the panels together so as to self-align in three directions along vertical, horizontal, and the central axes, and will releasably hold the panels together, and that the connectors on adjacent panels will align with the first ends of the opposed cylindrical pins in contact with one another under spring bias providing operative electrical connection between adjacent panels.

10. The modular instrumented floor covering assembly of claim 9, further comprising:
at least one inert panel having one interlocking edge, the inert panel being adapted for interlocking with one of the sensor panels along the interlocking edge, the inert panel having a beveled edge along remaining edges so as to preclude tripping the subject, the inert panel being adapted for guiding the subject toward the sensor panels;
a first magnet disposed on the interlocking edge of the inert panel, the first magnet having a north pole facing transversely outward and juxtaposed with the panel edge; and
a second magnet disposed on the interlocking edge of the inert panel, the second magnet having a south pole facing transversely outward and juxtaposed with the panel edge; wherein
the first magnet north pole of the inert panel being adapted for alignment with the second magnet south pole of the interlocking adjacent sensor panel; and
the second magnet south pole of the inert panel being adapted for alignment with the first magnet north pole of the interlocking adjacent sensor panel; so as to attract the inert panel and the sensor panel toward one another and juxtapose the inert panel and the sensor panel with one another and releasably attach the inert panel and the sensor panel to one another.

11. The modular instrumented floor covering assembly of claim 9, further comprising:
at least one edge panel having one interlocking edge, the edge panel being adapted for interlocking with one of the sensor panels along the interlocking edge, the edge panel having a beveled edge opposing the interlocking edge so as to preclude tripping the subject;
a first magnet disposed on the interlocking edge of the edge panel, the first magnet having a north pole facing transversely outward and juxtaposed with the panel edge; and
a second magnet disposed on the interlocking edge of the edge panel, the second magnet having a south pole facing transversely outward and juxtaposed with the panel edge; wherein
the first magnet north pole of the edge panel being adapted for alignment with the second magnet south pole of the interlocking adjacent sensor panel; and
the second magnet south pole of the edge panel being adapted for alignment with the first magnet north pole of the interlocking adjacent sensor panel; so as to attract the edge panel and the sensor panel toward one another and juxtapose the edge panel and the sensor panel with one another and releasably attach the edge panel and the sensor panel to one another.

12. The modular instrumented floor covering assembly of claim 11, wherein the power means further comprises:
at least one pair of electrical connectors disposed on the interlocking edge of the edge panel, a one of the pair being for positive voltage, and a remaining one of the pair being for negative voltage, the electrical connectors being adapted for operatively electrically and releasably connecting the electrical connectors on the edge panel to the electrical connectors on adjacent sensor panels, the connectors having a conductor on the edge panel interlocking edge adapted for contacting a conductor on the adjacent sensor panel interlocking edge with spring bias; and a power supply adapted for operatively electrically and releasably connecting the power source to the electrical connectors on the edge panel.

13. The modular instrumented floor covering assembly of claim 1, wherein each sensor panel further comprises:
   a flat bottom surface and an opposed flat top surface;
   a base layer sufficiently rigid to support the weight of the subject, the base layer extending upward from the bottom surface;
   a circuit layer extending upward from the base layer;
   a sensor matrix layer extending upward from the circuit layer; and
   a cover layer disposed above the sensor matrix layer, the cover layer being material adapted for walking upon; so that
   the cover layer will convey the weight of the subject to the sensor matrix layer, and the base layer will support the weight of the subject.

14. The modular instrumented floor covering assembly of claim 13, wherein each sensor panel further comprises:
   at least one circuit board immersed in the circuit layer and operatively electrically connected to the sensor matrix for collecting data from the sensor matrix; and
   the wireless means includes at least one wireless transceiver immersed in the circuit layer and operatively electrically connected to the circuit board for transmitting data wirelessly.

15. The modular instrumented floor covering assembly of claim 14, wherein the selective and releasable assembly in patterns further comprises patterns and enjoined combinations of patterns selected from the group consisting of:
   a straight pattern;
   a T-shaped pattern;
   an L-shaped pattern;
   a U-shaped pattern;
   an area pattern; and
   a perimeter pattern.

16. The modular instrumented floor covering assembly of claim 14, wherein the at least one wireless transceiver is immersed in the circuit layer and operatively electrically connected to the circuit board for transmitting data wirelessly, the wireless transceiver comprising a wireless local area network transceiver.

17. A modular instrumented floor covering assembly for use in connection with a subject walking across the assembly for generating data relating to movement of the subject, a power source, and a computer, the floor covering assembly comprising:
   a plurality of sensor panels having interlocking edges, the sensor panels being adapted for interlocking adjacent panels together along the edges, each sensor panel having a pressure sensor matrix responsive to a weight of the subject, the plurality of sensor panels being adapted for selective and releasable assembly in patterns;
   a first magnet disposed on each interlocking edge of each sensor panel, the first magnet having a north pole facing transversely outward from the panel edge and juxtaposed with the panel edge;
   a second magnet disposed on each interlocking edge of each sensor panel, the second magnet having a south pole facing transversely outward from the panel edge and juxtaposed with the panel edge; wherein
   the first magnet north pole of each sensor panel being adapted for alignment with the second magnet south pole of an interlocking adjacent panel; and the second magnet south pole of each sensor panel being adapted for alignment with the first magnet north pole of the interlocking adjacent panel; so as to attract the sensor panels toward one another and juxtapose the sensor panels with one another and releasably attach the sensor panels to one another;
   a wireless transceiver for communicating data from the sensor panels and between adjacent sensor panels; and
   at least one pair of electrical connectors disposed on each edge of each of the sensor panels, a one of the pair being for positive voltage, and a remaining one of the pair being for negative voltage, the connectors on adjacent sensor panels being adapted for operatively electrically and releasably connecting together upon interlocking adjacent panels together along the edges, the connectors having a conductor on the sensor panel interlocking edge adapted for contacting a conductor on the adjacent sensor panel interlocking edge with spring bias.

18. A method for assembling a modular instrumented floor covering assembly and generating data relating to movement of a subject walking across the assembly, for use in connection with a power source and a computer, the method comprising:
   interlocking a plurality of sensor panels releasably together along interlocking edges, forming the floor covering assembly;
   assembling the plurality of sensor panels selectively in patterns, forming a modular assembly;
   providing each sensor panel with a pressure sensor matrix responsive to a weight of the subject for generating data relating to movement of the subject;
   communicating data from the sensor panels and between adjacent sensor panels with a wireless transceiver;
   disposing a first magnet on each interlocking edge of each sensor panel;
   facing a north pole of the first magnet transversely outward from the panel edge;
   disposing a second magnet on each interlocking edge of each sensor panel;
   facing a south pole the second magnet transversely outward from the panel edge;
   aligning the first magnet north pole of each sensor panel with the second magnet south pole of an interlocking adjacent panel;
   attracting the sensor panels toward one another with the first and second magnets;
   aligning the sensor panels with one another with the first and second magnets; and
   releasably attaching the sensor panels to one another with the first and second magnets.

19. The method of claim 18, further comprising:
   disposing at least one pair of electrical connectors on each edge of each of the sensor panels;
   adapting one of the electrical connectors for positive voltage;
   adapting one of the electrical connectors for negative voltage;
   releasably connecting the connectors on adjacent sensor panels together operatively electrically upon interlocking adjacent panels together along the edges;
   providing each connector with a conductor on the sensor panel edge;
   supplying power from the power source to the sensor panels and between adjacent sensor panels with the conductors; and contacting conductors on adjacent sensor panels with spring bias.

20. The method of claim 19, further comprising:
connecting a power supply operatively electrically and releasably between the power source and the electrical connectors; and
converting line power AC to low voltage DC with the power supply.

21. The method of claim 20, further comprising:
forming a bore through the first magnet;
receiving one of the electrical connectors in the first magnet bore;
forming a bore through the second magnet;
receiving one of the electrical connectors in the second magnet bore; and
projecting each connector outward beyond the respective magnet, allowing contact with a corresponding connector on an adjacent sensor panel.

22. The method of claim 21, further comprising:
forming each magnet as toroidal in shape with a central axis;
aligning the north and south poles of the first magnet with the central axis;
aligning the first magnet bore with the first magnet central axis;
aligning the north and south poles of the second magnet with the central axis;
aligning the second magnet bore with the second magnet central axis;
forming the conductor by extending a cylindrical pin between a first end and a second end;
aligning the cylindrical pin with the magnet central axis;
receiving the cylindrical pin in the magnet bore;
projecting the cylindrical pin first end outward beyond the magnet; and
biasing the cylindrical pin in the direction of the first end with the spring.

* * * * *